(12) United States Patent
Kompella et al.

(10) Patent No.: US 8,067,422 B2
(45) Date of Patent: Nov. 29, 2011

(54) CRYSTAL FORM OF PHENYLAMINO PYRIMIDINE DERIVATIVES

(75) Inventors: Amala Kishan Kompella, Hyderabad (IN); Bhujanga Rao Adibhatla Kali Satya, Hyderabad (IN); Sreenivas Rachakonda, Hyderabad (IN); Nannapaneni Venkaiah Chowdary, Hyderabad (IN)

(73) Assignee: Natco Pharma Limited, Andhra Pradesh (IN)

( * ) Notice: Subject to any disclaimer, the term of this patent is extended or adjusted under 35 U.S.C. 154(b) by 921 days.

(21) Appl. No.: 12/042,247

(22) Filed: Mar. 4, 2008

(65) Prior Publication Data

US 2009/0227611 A1    Sep. 10, 2009

(51) Int. Cl.
*A01N 43/54* (2006.01)
*C07D 239/00* (2006.01)
*C07D 239/02* (2006.01)

(52) U.S. Cl. ............... 514/256; 544/242; 544/323
(58) Field of Classification Search ............... 544/242, 544/323; 514/256
See application file for complete search history.

(56) References Cited

FOREIGN PATENT DOCUMENTS

| WO | WO 99/15164 A | 4/1999 |
| WO | WO 2004/029038 A | 4/2004 |
| WO | WO 2004/110452 A | 12/2004 |
| WO | 2006/027795 * | 3/2006 |
| WO | WO 2006/027795 A1 | 3/2006 |

OTHER PUBLICATIONS

Invitation to Pay Additional Fees with Partial International Search mailed Jul. 15, 2009.
Ogata et al. "Synthesis and Antiviral activity of sulphonamidobenzophenone oximes and sulphonamidobenzamides." *Journal of Medicinal Chemistry*. vol. 29, No. 3. 1986. pp. 417-423.
Zimmermann et al. "Potent and selective inhibitors of the Abl-kinase: Phenylaminopyrimidine (PAP) derivatives." *Bioorganic and Medicinal Chemistry Letters*. vol. 7, No. 2. 1997. pp. 187-192.
Schindler et al. "Structural mechanism for STI-571 inhibition of Abelson tyrosine kinase." *Science*. vol. 289, No. 5486. 2000. pp. 1938-1942.
Caira, M., "Crystalline Polymorphism of Organic Compounds," *Topics in Current Chemistry*, vol. 198, pp. 163-208 (1998).
International Search Report and Written Opinion mailed Oct. 29, 2009.
Paquette, L. (Editor), "Tin(II) Chloride," *Encyclopedia of Reagents for Organic Synthesis*, pp. 4892-4893 (1995).

* cited by examiner

*Primary Examiner* — Paul V. Ward
(74) *Attorney, Agent, or Firm* — Merchant & Gould P.C.

(57) ABSTRACT

The present invention relates to a particular form of the (3,5-bis trifluoromethyl)-N-[4-methyl-3-(4-pyridin-3yl-pyrimidin-2ylamino)-phenyl]-benzamide (formula I), processes for the preparation thereof, pharmaceutical compositions containing this crystal form, and their use as anti tumor agent in humans. The compound of formula I, also known as AN-019, is:

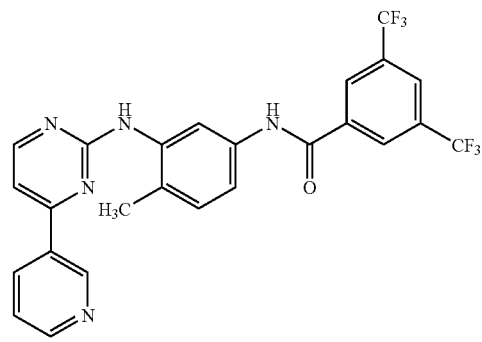

Development code: AN-019

12 Claims, 25 Drawing Sheets

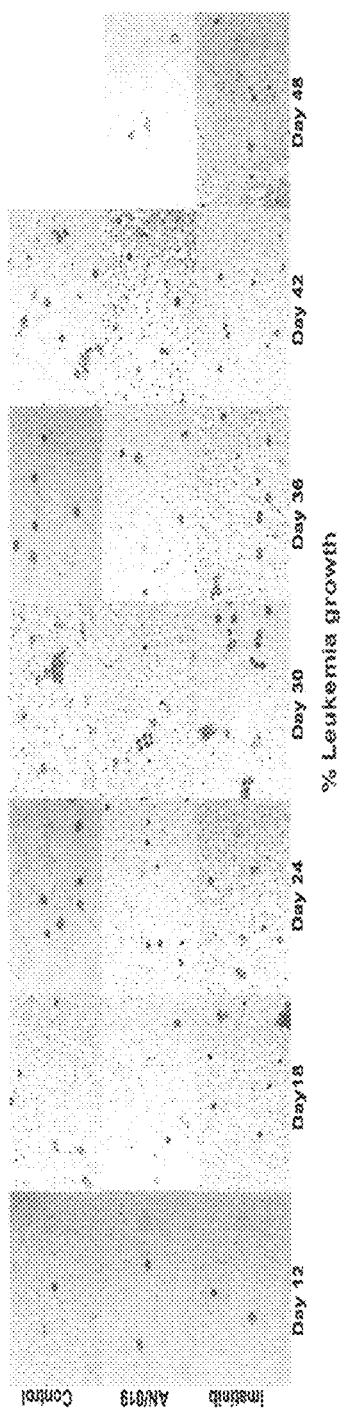
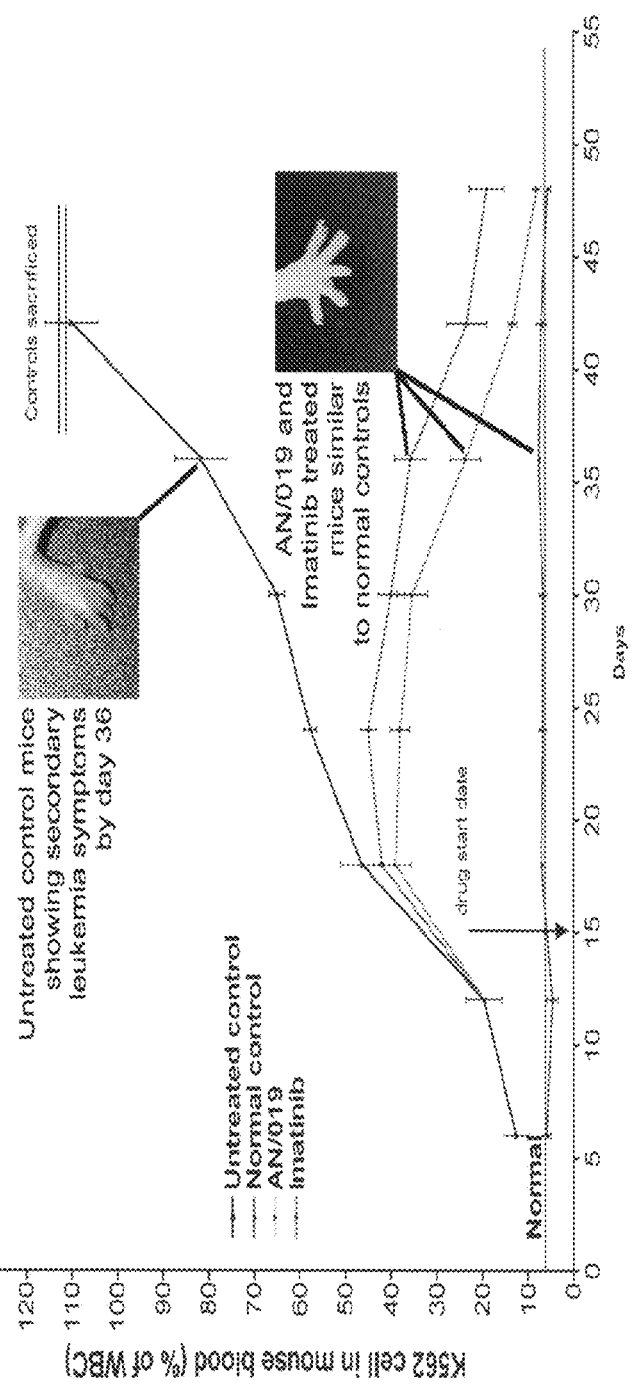
FIG. 10A
FIG. 10B

Western blot analysis

CRYSTAL FORM OF PHENYLAMINO PYRIMIDINE DERIVATIVES

FIELD OF THE INVENTION

The present invention relates to a particular form of the (3,5-bis trifluoromethyl)-N-[4-methyl-3-(4-pyridin-3yl-pyrimidin-2ylamino)-phenyl]-benzamide (formula I), processes for the preparation thereof, pharmaceutical compositions containing this crystal form, and their use as anti tumor agent in humans. The compound of formula I, also known as AN-019, is:

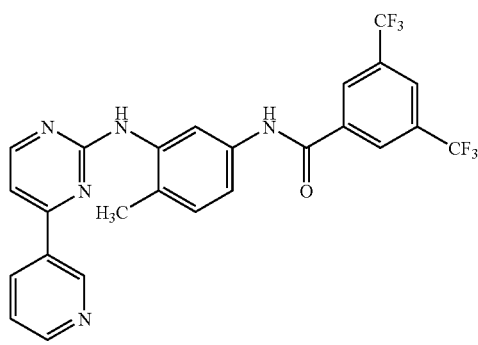

Development code: AN-019

Formula-I

BACKGROUND OF THE INVENTION

The preparation of (3,5-bis trifluoromethyl)-N-[4-methyl-3-(4-pyridin-3yl-pyrimidin-2ylamino)-phenyl]-benzamide of formula I, and the use thereof, especially as an anti-tumour agent, are described in Examples 3 and 4 of WO2006/027795 (PCT/IN05/00243 filed Jul. 19, 2005) which was published on 16 Mar. 2006, and in corresponding applications in numerous other countries including USA (Pub. No.: US 2007/0232633). In these publications polymorphism is not discussed.

It has now been surprisingly found that under certain conditions a new polymorphic form of the compound of formula I is formed, which is described hereinafter as Form-III crystal form, and it has advantageous properties.

SUMMARY OF THE INVENTION

The present invention relates to a particular form of the (3,5-bis trifluoromethyl)-N-[4-methyl-3-(4-pyridin-3yl-pyrimidin-2ylamino)-phenyl]-benzamide (formula I), processes for the preparation thereof, pharmaceutical compositions containing this crystal form, and their use as anti tumor agent in humans. The compound of formula I, also known as AN-019, is:

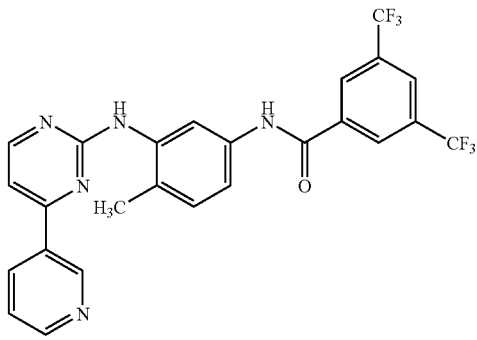

In an embodiment, the present invention relates to a Form-III crystal form of (3,5-bis trifluoromethyl)-N-[4-methyl-3-(4-pyridin-3yl-pyrimidin-2ylamino)-phenyl]-benzamide (formula I), wherein the Form-III crystal form has the XRPD characteristics listed in Table 3, below. This crystal form can have a melting point at or above 240° C. The crystal form can be essentially pure.

In an embodiment, the present invention relates to a method of treating a subject in need of anti-proliferative therapy. This embodiment of the method can include administering to the subject a Form-III crystal form of (3,5-bis trifluoromethyl)-N-[4-methyl-3-(4-pyridin-3yl-pyrimidin-2ylamino)-phenyl]-benzamide (formula I), wherein the Form-III crystal form has the XRPD characteristics listed in Table 3, below.

The present invention also relates to a pharmaceutical composition. The pharmaceutical composition includes a pharmaceutically acceptable excipient and a Form-III crystal form of (3,5-bis trifluoromethyl)-N-[4-methyl-3-(4-pyridin-3yl-pyrimidin-2ylamino)-phenyl]-benzamide (formula I), wherein the Form-III crystal form has the XRPD characteristics listed in Table 3, below.

The present invention also relates to a use of a Form-III crystal form of (3,5-bis trifluoromethyl)-N-[4-methyl-3-(4-pyridin-3yl-pyrimidin-2ylamino)-phenyl]-benzamide (formula I), wherein the Form-III crystal form has the XRPD characteristics listed in Table 1 below for producing an anti-proliferative medicament for treating a tumor disorder.

The present invention relates to a process for preparing a Form-III crystal form of (3,5-bis trifluoromethyl)-N-[4-methyl-3-(4-pyridin-3yl-pyrimidin-2ylamino)-phenyl]-benzamide (formula I), wherein the Form-III crystal form has the XRPD characteristics listed in Table 3, below. This process includes treating the compound of formula I in a Form-I or Form-II crystal form with acetic acid or a mixture of dimethyl formamide and acetone, hexane, or toluene. This process can also include subsequently treating the once treated compound with acetic acid, acetone, hexane, or toluene.

In another aspect, the present invention relates to a Form-I crystal form of (3,5-bis trifluoromethyl)-N-[4-methyl-3-(4-pyridin-3yl-pyrimidin-2ylamino)-phenyl]-benzamide (formula I), wherein the Form-I crystal form has the XRPD characteristics listed in Table 1, below.

In another aspect, the present invention relates to a Form-II crystal form of (3,5-bis trifluoromethyl)-N-[4-methyl-3-(4-pyridin-3yl-pyrimidin-2ylamino)-phenyl]-benzamide (formula I), wherein the Form-II crystal form has the XRPD characteristics listed in Table 2, below.

BRIEF DESCRIPTION OF THE FIGURES

The patent application file contains at least one drawing executed in color. Copies of this patent or patent application

FIGS. 10A and 10B illustrate that intraperitoneal injections of the compound of formula I (Example 1) caused regression of leukemia in nude mice. Tail vein drawn blood smears revealed an increase in LGI in controls and a progressive decrease in LGI in Imatinib- and AN019-treated mice (FIG. 10A). On day 48 LGI of Imatinib-treated mice was determined to be 20±5, whereas LGI of AN019-treated mice was found to be 10±2 with an almost normal cell count (FIG. 10B).

DETAILED DESCRIPTION

Figure 1:
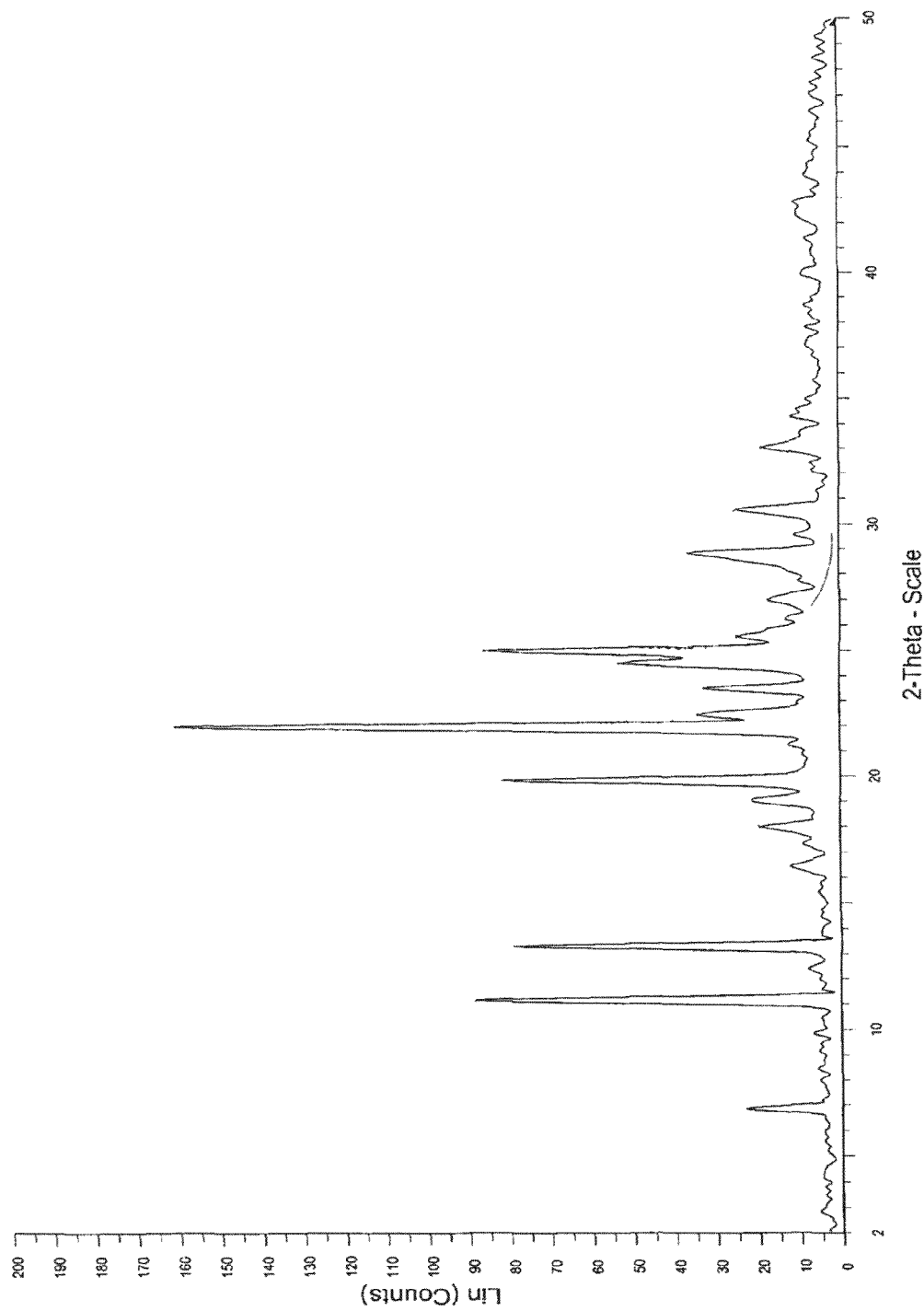
FIG. 1 shows the X-ray diffraction (XRD) diagram of the Form-I crystal form of the compound of formula I. The 2θ values and intensities are tabulated in Table 1.

Table 1 shows 2θ values and intensities of the Form-I crystal form of the compound of formula I from the X-ray diffraction (XRD) diagram of FIG. 1.

TABLE 1

| (Form-I) | | |
|---|---|---|
| Angle [2-Theta] | d-value Angstrom | Intensity % |
| 6.793 | 13.00131 | 13.9 |
| 9.823 | 8.99680 | 3.9 |
| 11.106 | 7.96069 | 54.2 |
| 13.267 | 6.66829 | 48.5 |
| 16.386 | 5.40523 | 7.0 |
| 17.941 | 4.94015 | 11.3 |
| 18.997 | 4.66785 | 13.0 |
| 19.778 | 4.48530 | 50.5 |
| 21.894 | 4.05635 | 100.0 |
| 22.396 | 3.96650 | 20.5 |
| 23.469 | 3.78750 | 19.7 |
| 24.466 | 3.63545 | 32.4 |
| 24.939 | 3.56759 | 52.6 |
| 25.525 | 3.48695 | 14.6 |
| 26.968 | 3.30351 | 10.3 |
| 28.777 | 3.09991 | 22.0 |
| 30.545 | 2.92436 | 14.8 |
| 33.011 | 2.71129 | 11.0 |

Figure 2:
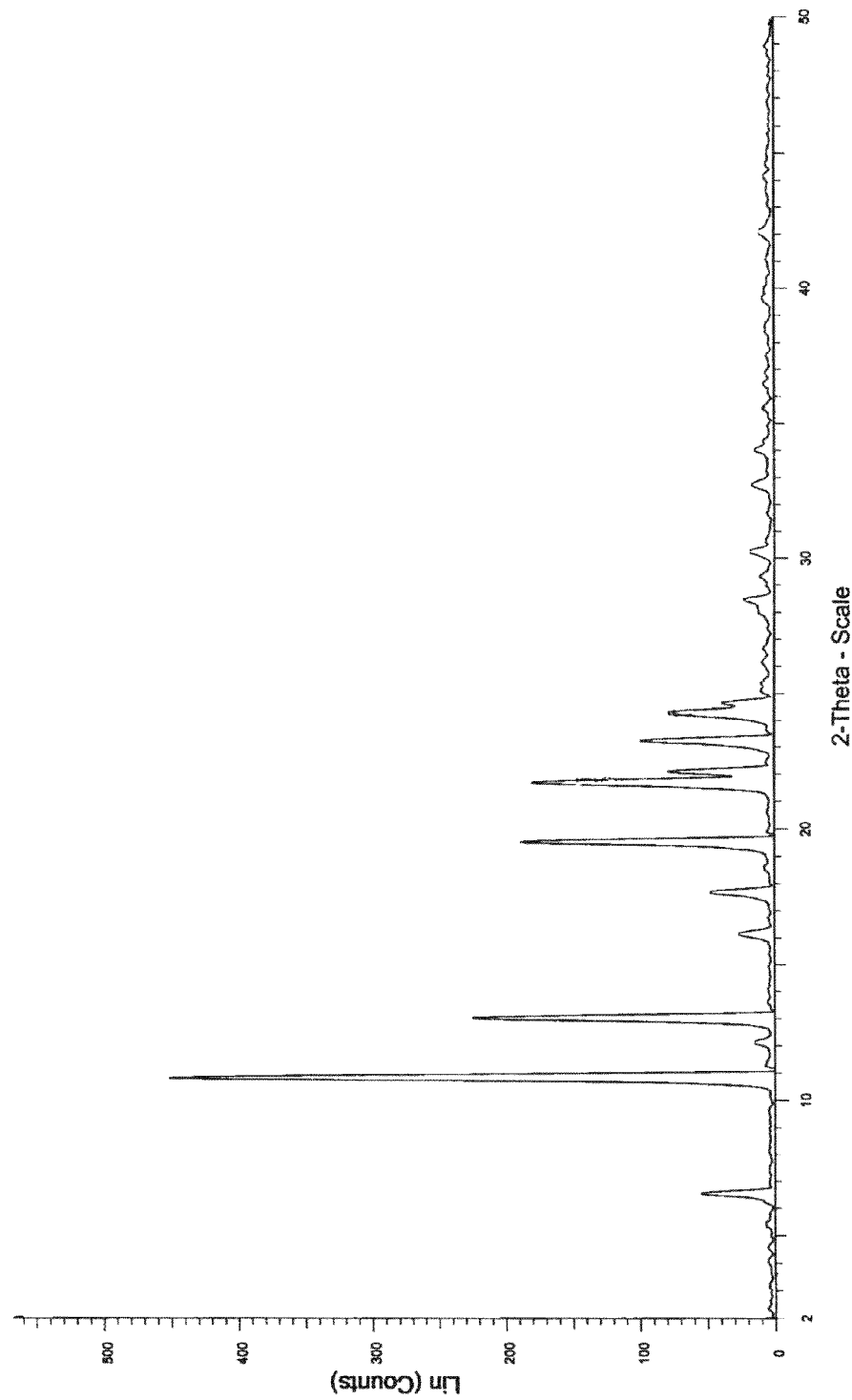
FIG. 2 shows the X-ray diffraction (XRD) diagram of the Form-II crystal form of the compound of formula I. The 2θ values and intensities are tabulated in Table 2.

Table 2 shows 2θ values and intensities of the Form-II crystal form of the compound of formula I from the X-ray diffraction (XRD) diagram of FIG. 2.

TABLE 2

| (Form-II) | | |
|---|---|---|
| Angle [2-Theta] | d-value Angstrom | Intensity % |
| 6.500 | 13.58651 | 12.2 |
| 10.816 | 8.17295 | 100.0 |
| 12.094 | 7.31197 | 3.4 |
| 12.988 | 6.81061 | 49.7 |
| 16.120 | 5.49381 | 6.0 |
| 17.669 | 5.01562 | 10.9 |
| 19.521 | 4.54367 | 41.7 |
| 21.675 | 4.09687 | 39.9 |
| 22.083 | 4.02198 | 17.1 |
| 23.230 | 3.82602 | 21.9 |
| 24.264 | 3.66523 | 17.8 |
| 24.639 | 3.61023 | 8.5 |
| 28.460 | 3.13371 | 4.8 |
| 29.328 | 3.04290 | 2.3 |

TABLE 2-continued (Form-II)

| Angle [2-Theta] | d-value Angstrom | Intensity % |
|---|---|---|
| 30.256 | 2.95165 | 4.1 |
| 32.746 | 2.73261 | 3.5 |
| 34.035 | 2.63201 | 3.1 |
| 35.590 | 2.52050 | 1.5 |
| 39.660 | 2.27072 | 1.9 |
| 42.123 | 2.14346 | 2.5 |
| 44.193 | 2.04777 | 1.7 |

Figure 3:
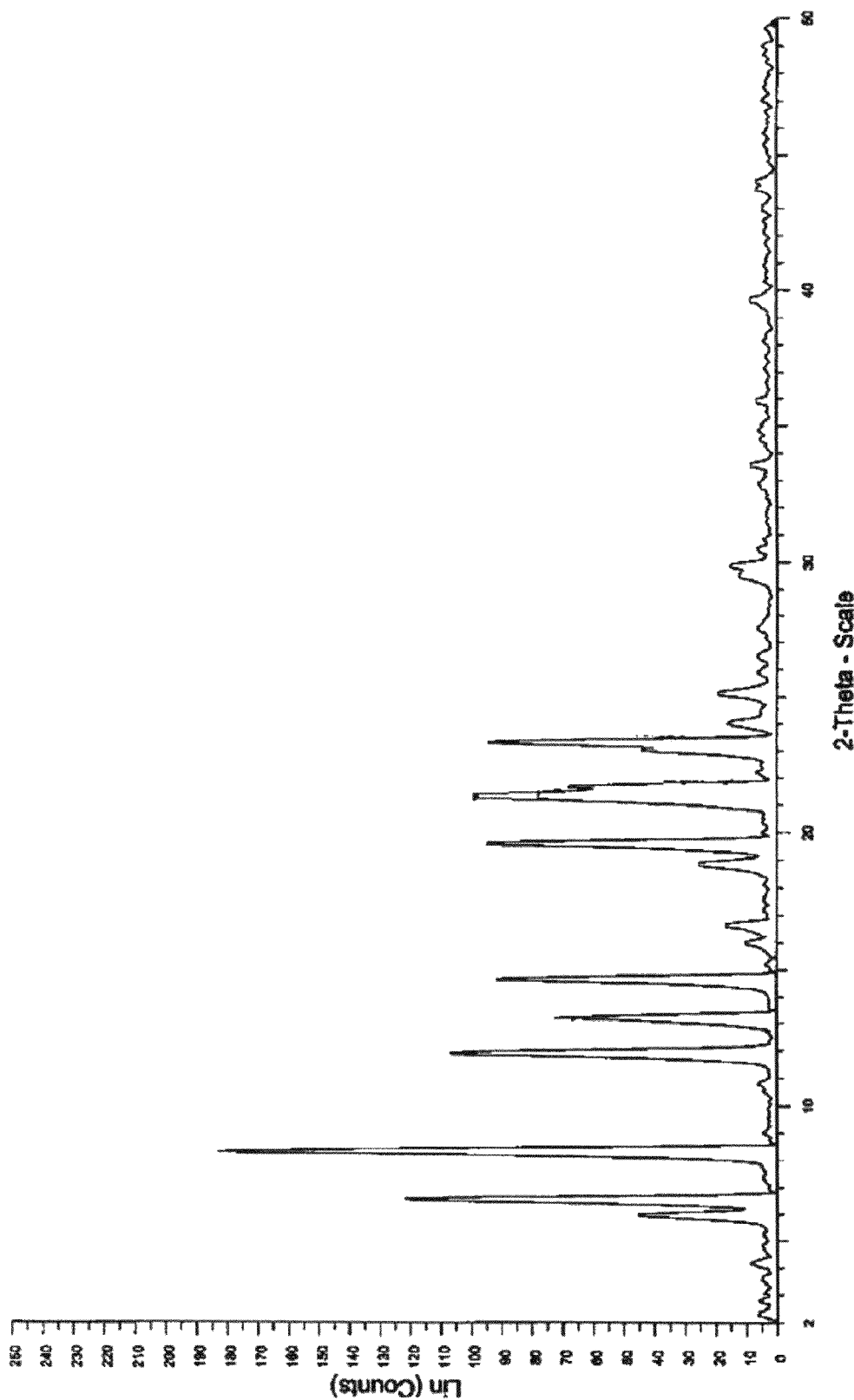
FIG. 3 shows the X-ray diffraction (XRD) diagram of the Form-III crystal form of the compound of formula I. The 2θ values and intensities are tabulated in Table 3.

Table 3 shows 2θ values and intensities of the Form-III crystal form of the compound of formula I from the X-ray diffraction (XRD) diagram of FIG. 3.

TABLE 3

(Form-III)

| Angle [2-Theta] | d-value Angstrom | Intensity % |
|---|---|---|
| 5.909 | 14.94417 | 24.9 |
| 6.491 | 13.60517 | 66.4 |
| 8.267 | 10.68690 | 100.0 |
| 11.854 | 7.45967 | 58.2 |
| 13.181 | 6.71147 | 40.0 |
| 14.609 | 6.05866 | 50.0 |
| 15.960 | 5.54851 | 5.8 |
| 16.612 | 5.33224 | 9.5 |
| 18.826 | 4.70995 | 14.4 |
| 19.571 | 4.53226 | 52.1 |
| 21.302 | 4.16774 | 54.0 |
| 21.612 | 4.10861 | 37.7 |
| 22.160 | 4.00828 | 3.5 |
| 22.970 | 3.86869 | 23.8 |
| 23.278 | 3.81812 | 51.6 |
| 24.000 | 3.70491 | 8.7 |
| 25.112 | 3.54329 | 11.1 |
| 25.887 | 3.43895 | 3.1 |
| 26.500 | 3.36079 | 3.3 |
| 27.517 | 3.23887 | 3.4 |
| 29.476 | 3.02788 | 6.8 |
| 29.857 | 2.99011 | 8.6 |
| 30.474 | 2.93102 | 3.5 |
| 32.886 | 2.72133 | 3.2 |
| 33.559 | 2.66829 | 5.0 |
| 35.916 | 2.49836 | 3.8 |
| 39.645 | 2.27157 | 4.9 |
| 43.061 | 2.09893 | 2.6 |
| 43.748 | 2.06753 | 3.8 |
| 44.055 | 2.05383 | 3.9 |

The Form-III crystal form of the compound of formula I is characterized by needle-shaped crystals. The Form-I and Form-II crystal forms of the compound of formula I are characterized by non-needle shaped crystals The Form-I and Form-II crystal forms of the compound of formula I are metastable at room temperature. However, the Form-III crystal form of the compound of formula I is the thermodynamically stable form at room temperature. This is indicative of the greater stability of the Form-III crystal form.

Accordingly, in an embodiment the present invention provides a Form-III crystalline form of the compound of formula I which is stable at room temperature and even at higher temperatures (e.g., 120° C.) and accelerated stress conditions, and having the characteristics given in Table 3 (above).

In an embodiment, the present invention provides a process for the preparation of Form-III crystal form of the compound of formula I which is stable and has the characteristics given in Table 3.

Table 4 shows the heat stability of Form-III crystal form at temperatures of 110-140° C. The Form-III was shown to be non-metastable and stable when heated at 130° C. for 6 hours.

Pure Form-III crystal form (1 gm) prepared by the present process was placed in a boiling tube and heated gradually in oil bath. Then the substance was examined by XRPD. The results are tabulated in Table 4.

TABLE 4

| Polymorph content* before heating | Temperature | Time of heating (hours) | Polymorph form detected* after heating |
|---|---|---|---|
| Form-III | 110° C. | 6 | Form-III |
| Form-III | 120° C. | 6 | Form-III |
| Form-III | 130° C. | 6 | Form-III |

*The presence of form-I and Form-II was below the detection level in these examples.

This data demonstrates that the Form-III crystal form was not metastable. The Form-III crystal form was stable to heat even at 130° C. for 6 hours.

Table 5 shows the stability of Form-III crystal form under accelerated stress conditions (45±2° C., 75±5% RH, 6 months) in the bulk and capsule formulation.

TABLE 5

Stability of Form-III crystal form in bulk and formulated capsule

| Polymorph content* of Formula I in formulated capsule | Polymorph content* of bulk compound of formula I | Duration of storage (months) at 40 ± 2° C./75 ± 5% RH |
|---|---|---|
| Polymorph form detected | Polymorph form detected | |
| Form-III | Form-III | 0 Month |
| Form-III | Form-III | 1 Month |
| Form-III | Form-III | 2 Months |
| Form-III | Form-III | 3 Months |
| Form-III | Form-III | 6 Months |

*The presence of form-I and form-II was below the detection level in these examples.

This data demonstrates that form-III is not converted to other forms over a time period. The stability of form III in bulk and in the formulated capsule was thus established.

In an embodiment, the present invention provides a pharmaceutical composition useful for the tumor therapy containing the stable Form-III crystal form of the compound of formula I.

The dosage form of the formulation containing the stable Form-III crystal form, which can be prepared by the process of the present invention, for example, an oral dosage form, may be a capsule containing the composition, e.g., a powdered or granulated solid composition, within either a hard or soft shell. The shell may be made from gelatin that optionally contains a plasticizer, such as glycerin or sorbitol, and an opacifying agent or colorant.

Methods known in the art may be used to prepare the pharmaceutical composition containing Form-III crystal form in the form of capsules. The excipients which may be employed include micro crystalline cellulose, poloxamer 407, crospovidone XL, Aerosil, SLS, magnesium stearate, or mixture thereof.

Table-6 shows suitable amounts of active ingredients and excipients (weight %) for the present pharmaceutical formulations.

TABLE 6

An embodiment of a pharmaceutical composition containing the Form-III crystal form

| S. No. | Material | composition (w/w) mg/capsule |
|---|---|---|
| 1. | Compound of Formula I, Form-III | 25.0 |
| 2. | Micro crystalline cellulose | 8.0 |
| 3. | Poloxamer 407 | 12.5 |
| 4. | Crospovidone XL | 12.5 |
| 5. | Magnesium stearate | 0.5 |
| 6. | SLS | 4.0 |
| 7. | Aerosil | 0.25 |

In an embodiment, the invention relates to a particular, essentially pure Form-III crystal form of (3,5-bis trifluoromethyl)-N-[4-methyl-3-(4-pyridin-3yl-pyrimidin-2ylamino)-phenyl]-benzamide (formula I). The term "essentially pure" is understood in the context of the present invention to mean that about 90 to 100 wt-%, about 95 to 100 wt-%, or, for example, about 99 to 100 wt-% of the crystals of formula I are present in the crystal form according to the invention, e.g., the Form-III crystal form.

In the context of stating that the Form-III crystal form of formula I exhibits an X-ray diffraction diagram essentially as in FIG. 3, the term "essentially" means that at least the major lines of the diagram depicted in FIG. 3, i.e. those having a relative line intensity of more than 10%, especially more than 20%, as compared to the most intense line in the diagram, are present.

The crystal forms have the following properties:

The melting point in the DSC thermogram of the Form-III crystal form is 246.7° C. The melting point in the DSC thermogram of the Form-I crystal form is 234° C. and Form-II crystal form is 240.47° C., 249.2° C. (peak).

The X-ray diffraction diagrams also show other marked differences. In an embodiment, the essentially pure Form-III crystal form of the compound of formula I shows the X-ray diffraction diagram indicated in FIG. 3.

Figure 9:
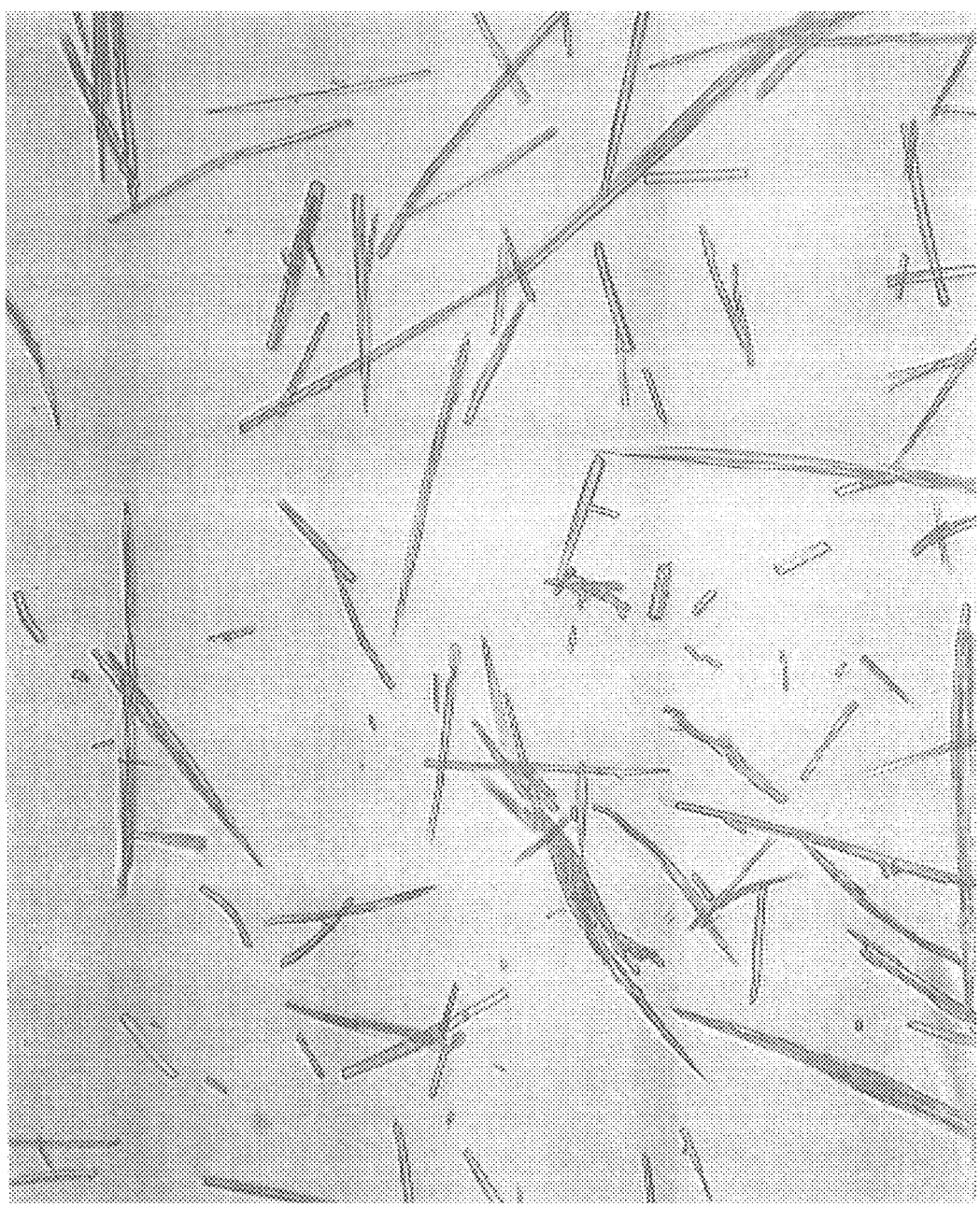
FIG. 9 shows morphology of Form-III crystal form of the compound of formula I.

In an embodiment, the invention relates to the Form-III crystal form of the compound of formula I which is characterised by the presence of crystals displaying the form shown in FIG. 9, for example, the Form-III crystal form in essentially pure form.

In an embodiment, the Form-III crystal form of the compound of formula I has a melting point of higher than 240° C., e.g., between 245 and 250° C.

The (for example, essentially pure) Form-III crystal form is obtainable by the following method: Treating another crystal form, e.g., the Form-I or Form-II crystal form, of the compound of formula I, with a suitable polar solvent, e.g., N,N-di-lower alkyl-lower alkanecarboxamide, such as N,N-dimethylformamide or N,N-dimethylacetamide, or, e.g., an aliphatic carboxylic acid such as acetic acid, or a mixture of the above with a ketone, such as acetone, or a hydrophobic hydrocarbon, e.g., toluene or hexane, or a mixture thereof, at a suitable temperature.

In an embodiment, the compound of formula I is treated with a mixture of dimethyl formamide and acetone followed by treatment in acetone. In an embodiment, the compound of formula I is treated with a mixture of dimethyl formamide and hexane followed by treatment in hexane. In an embodiment, the compound of formula I is treated with a mixture of dimethyl formamide and toluene followed by treatment in toluene. In an embodiment, the compound of formula I is treated one or more times with acetic acid. In this context, treating or treatment refers to heating, cooling, refluxing, washing, suspending, or the like in the solvent or mixture of solvents. These embodiments each yield the Form-III crystal form of the compound of formula I.

In certain embodiments, the present method of producing the Form-III crystal form of does not include treating another crystal form of the compound of formula I with chloroform, methanol, dichloromethane, ether (e.g., diethyl ether), water, ethyl acetate, or mixture thereof. In certain embodiments, the Form-III crystal form was not produced by treating another crystal form of the compound of formula I with chloroform, methanol, dichloromethane, ether (e.g., diethyl ether), water, ethyl acetate, or mixture thereof.

Form-III crystal form of the compound of formula I as well as other forms possess useful pharmacological properties and may, for example, be used as anti-tumour agents.

The present invention also includes a method of preparing compound of formula I. This method can include:

providing a compound of formula VI, 3,5-bis trifluoro methyl benzoyl chloride; or preparing this compound by known methods;

condensing 4-methyl-3-nitro-aniline with the compound of formula (IV) at about 0 to about −10° C. in chlorohydrocarbon solvent with addition of a basic compound to obtain a compound of formula III, ((3,5-bis trifluoromethyl)-N-(4-methyl-3-nitrophenyl)-)-benzamide;

reducing the compound of formula (III) with stannous chloride/conc. HCl at reflux temperature for about 0.5 to about 1 hour to obtain a compound of formula IV, (3,5-bis trifluoromethyl)-N-(3-amino-4-methylphenyl)-)-benzamide;

condensing the compound of formula IV with aqueous cyanamide at reflux temperature in n-butanol solvent to obtain a compound of formula V, (3,5-bis-trifluoromethyl)-N-(3-guanidino-4-methylphenyl)-benzamide;

condensing the compound of formula (V) with 3-dimethylamino-1-pyridin-3-yl-propenone in presence of base at reflux temperature to obtain the compound of formula (I). In an embodiment, the method is accomplished as described in Example 10.

The disclosures of U.S. patent application Ser. No. 11/714,565, filed Mar. 5, 2007 (U.S. Publication No. US 2007/0232633, published on Oct. 4, 2007) and of PCT Application No. PCT/IN 2005/000243, filed Jul. 19, 2005 (PCT Publication No. WO2006/027795, published on Mar. 16, 2006) are incorporated by reference herein in their entirety.

Embodiments of the present invention are described in the examples given below, which are provided to illustrate the invention only and therefore they should not be construed to limit the scope of the invention.

EXAMPLES

General Note

The principal compound of this invention of formula I (Indicated by development code AN-019) is found to exhibit useful anti-tumor activity superior to some of the existing approved drugs of this class. This compound is found to exhibit in three distinct polymorphic forms I, II and III as discussed above. Although all the forms exhibit valuable pharmacological properties and may be used as anti-tumor agents Form III was chosen for the biological activity evaluation based on its thermodynamic stability. The development code AN-024 refers to another compound of the same class described elsewhere by the inventors. The bio-efficacy and activity of the compounds of this invention have been compared with the approved drugs like Imatinib mesylate and Dasatinib to serve as positive controls in this study. 'Imatinib mesylate' has been abbreviated and referred to as 'Imatinib' in this study.

Example 1

Establishment of Anti-CML Activity of AN-019 in Nude Mice Implanted with k562 Cells (FIGS. 10A and 10B)

To determine anti-CML activity of compounds of this invention K562 cells were obtained from ATCC and nude mice were implanted with these cells. As control, Imatinib was used at the same concentration per kg body weight for comparison. Drug treatment was initiated 15 days post implantation and for 48 days with daily ip injections of 10 mg/kg. Blood was drawn from the tail vein every $6^{th}$ day, percent K562 cells determined and percent leukemia growth index (LGI) calculated.

AN019-treated mice showed a steady decline in LGI after initiation of drug treatment. LGI for Imatinib-treated mice also showed a decline but significantly lagged AN019 treated mice. Forty-eight days after continuous ip injections, AN019-treated mice were comparable to normal control mice, and Imatinib-treated mice showed an LGI of 20±5 when compared to controls. Spleen immunohistochemistry for Crk protein reveled localization of K562 cells in the spleen in control mice. AN019-treated mice showed basal levels of Crk expression, whereas Imatinib treated mice showed few colonies with low to undetectable expression levels of Crk.

Methods

K562 Implantation

Nude mice (nu/nu) were implanted with K562 cells ($1\times10^6$) via tail vein. Four mice were used per group and divided into 4 groups. Three groups were implanted with K562 cells and one group was used as normal controls. Group 2 was inoculated with K562 cells and served as untreated positive controls. Two other groups implanted with K562 cells were treated with either Imatinib or AN019.

IP Injection of AN019 and Imatinib

K562 implanted mice were treated with either Imatinib or AN019 (10 mg/Kg body wt) via intraperitoneal injections. Stock solutions of Imatinib and AN019 were made at a concentration of 100 µg/µl in DMSO. Mice were injected via an intraperitoneal route at the above-mentioned dosage. Average weight of nude mice was determined to be 30±3 g, and the dosage per mouse was calculated to be 300±30 µg/mouse. Three micro liters of the stock solutions was diluted to 100 µl with sterile water just prior to ip injections. Ip injections were carried out daily from day 15 post implantation to day 48 with a total of 33 injections.

Determination of Leukemia Growth Index (LGI)

Leukemia growth index was determined using the formula LGI (%)=$(V_c-V_t)V_c\times100\%$. $V_c$ is mean blast cell number (K562) per ml of blood in control animals at a certain time of measurement, and $V_t$ is mean blast cell number per ml of blood in test animals at a certain time of measurement. Blood was drawn from the mice (treated and untreated) on the sixth day post-K562 cell implantation and followed by an every six-day interval for 48 days. Blood was drawn via the tail vein. Quantitative analysis of LGI was graphically represented.

Immunocytochemistry

Control mice were sacrificed on day 42 when secondary leukemia symptoms were observed, such as abdominal swelling and lack of circulation in the peripherals causing loss of digits with red spots under the skin surface. Spleen and any secondary tumors were harvested, fixed in formaldehyde and paraffin embedded as per standard protocols. Paraffin section were obtained and processed for immunocytochemistry. The rehydrated sections were treated with 0.3% $H_2O_2$ to inactivate any native peroxidases prior to immuno-probing. The sections were blocked with filter sterilized (0.22 µm) 1% BSA-PBS at room temperature for 1 h. Following blocking, the sections were immuno-probed with a human specific anti-Crk monoclonal primary antibody raised in rabbit against a synthetic peptide corresponding to residues in the SH2 domain, near the N-term of human CrkL protein (Abcam, Cambridge, Mass., USA) in 1% BSA-PBS overnight. Secondary antibody (anti-rabbit) conjugated to HRP was used to detect the presence of primary antibody. The sections were briefly rinsed three times in PBS solution after immuno-probing with secondary antibody, and DAB HRP substrate was added per manufacture's instructions (Sigma St Louis Mo. USA). The reaction was allowed to proceed until sharp contrast between positive and negative controls was observed. For negative controls primary antibody were eliminated. Leukemic mice spleen served as positive controls.

Results

Intraperitoneal injections of AN019 caused regression of leukemia in nude mice. Blood smears taken every sixth day post-implantation indicated an increase in LGI in controls when compared to untreated mice. Tail vein drawn blood smears revealed an increase in LGI in controls and a progressive decrease in LGI in Imatinib- and AN019-treated mice (FIG. 10A). From the fifteenth day post-implantation, mice were given intraperitoneal injections of AN019 or Imatinib at a dosage of 10 mg/kg body weight. Imatinib-treated mice lagged AN019-treated mice at every data point. On day 48 LGI of Imatinib-treated mice was determined to be 20±5, whereas LGI of AN019-treated mice was found to be 10±2 with an almost normal cell count (FIG. 10B).

Example 2

Figure 11:
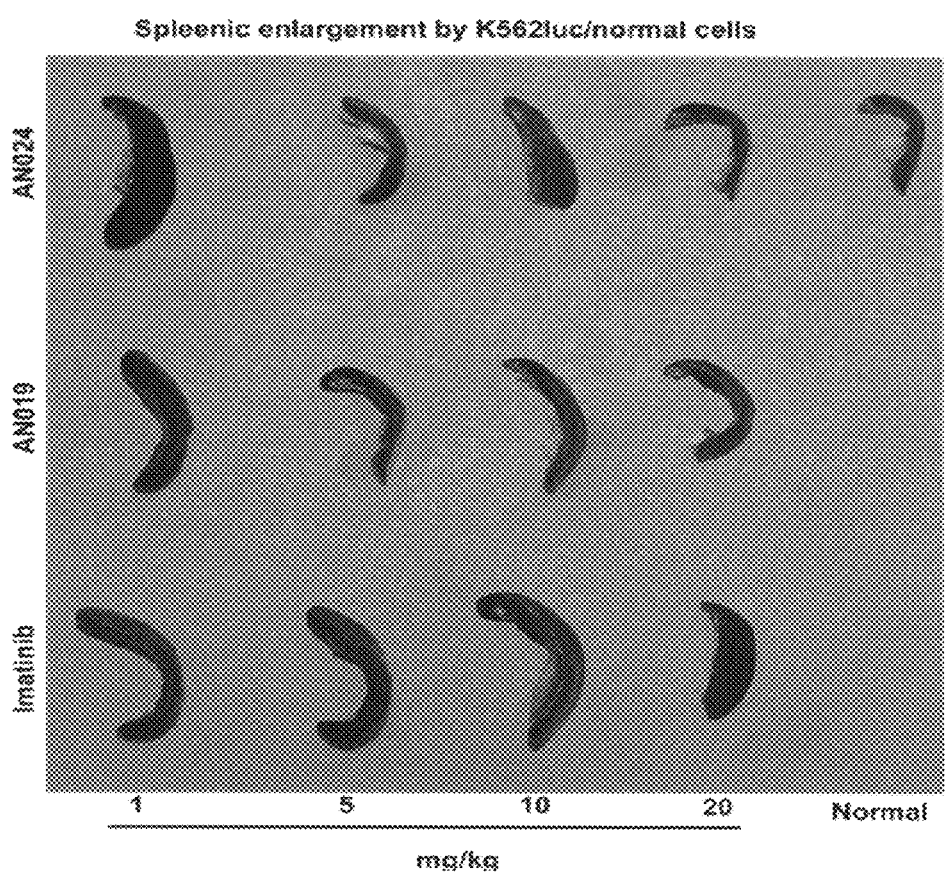
FIG. 11 illustrates that AN019-treated cells did not show any spleenic enlargement whereas Imatinib-treated mice showed spleenic enlargement (Example 2).

AN019 Injections of Nude Mice Implanted with K562 Cells did not Show Spleenic Enlargement and No Crk Expression (FIG. 11)

Nude mice implanted with K562 cells were treated with Imatinib or AN019 via ip injections. Mice were sacrificed after a decrease in LGI was observed and spleen harvested. Spleenic enlargement was observed by gross observation and it was determined that control mice showed enlarged spleen indicative of K562 cellular localization. AN019-treated cells did not show any spleenic enlargement whereas Imatinib-treated mice showed slight spleenic enlargement (FIG. 11). Paraffin sections of spleen immuno-probed for the presence of Crk protein showed strong localization of Crk expression accompanied with increased cellular density indicative of K562 localization in control mice. Mice treated with AN019 showed only basal level expression of Crk expression comparable to negative control. Mice treated with Imatinib indicated localized expression regions of Crk expression, indicative of K562 cells in the spleen. Control mice also developed random subcutaneous tumors showing Crk expression, indicative of the presence of K562 cells.

From these results it is evident that AN019 treatment caused the regression of LGI in nude mice. Imatinib-treated mice also showed significant reduction in LGI but lagged AN019-treated mice. Both AN019- and Imatinib-treated mice showed no abnormal physiological, phenotypic or behavioral abnormality. Control mice showed the presence of random subcutaneous tumors with loss of digits accompanied with reddish spots under the skin and a slight enlargement of the abdomen. From these results, it is evident that AN019 provides a promising therapeutic drug for the treatment of leukemia.

Example 3

In Vivo Studies Using Baf3 Imatinib Resistant Murine CML Cell Lines

To determine the in vivo anti-leukemic activity of AN019 and AN024, nude mice were implanted intraperitoneally with Baf3 murine leukemia cells (Wt, T315I, M351T and E225K), and 15 days after implantation the mice were treated with Imatinib (10 mg/kg), AN019 (20 mg/kg) and AN024 (20 mg/kg) by oral gavage or ip injections. Blood smears were obtained via the tail vein or via the femoral vein every 6th day and blast cells counted and graphically represented.

Blood smears of Baf3Wt implanted mice treated with Imatinib (10 mg/kg), AN019 (20 mg/kg) or AN024 (20 mg/kg) were similar to normal controls after 42 days.

Blood smears of Baf3T315I implanted mice treated with Imatinib (10 mg/kg), AN019 (20 mg/kg) or AN024 (20 mg/kg) showed a significant decrease in blast cell count in AN024 and AN019 treated mice. Mice treated with oral dosage of Imatinib did not show a decrease in blast cell count and were similar to untreated controls and Baf3M351T implanted mice.

Mice implanted with Baf3E255K also behaved similarly to Baf3M351T and Baf3T315I implanted mice.

Nude mice were implanted with Baf3 mutant cells Wt, E255K, T315I, and M351T were treated with Imatinib, AN019 and AN024 (orally and ip). Briefly, mice were treated with Imatinib (10 mg/kg), AN019 (20 mg/kg) and AN024 (20 mg/kg) by oral gavage or ip injections 15 days post-implantation. Abdominal swelling and decrease in activity was monitored daily, blood smear taken via the tail vein or the femoral vein every $6^{th}$ day and H&E stained as per standard protocols. 42 days after implantation, mice were sacrificed and spleens harvested. Spleenic enlargement was determined and correlated with blood smear blast cell count.

Results

Microscopic Determination of Blast Cell Count

Blood from tail vein or the femoral vein was taken every 6th day from Baf3 cell implanted mice until day 42. On the 15th day post-implantation, the mice were given treatments with Imatinib, AN019 and AN024 (orally and ip) as described earlier. It was observed that in Baf3Wt implanted mice, progressive decrease in blast cell count was observed in all treatment conditions. Baf3M351T, T315I and E225K did not respond well to Imatinib treatments. Oral administration of Imatinib had no significant effect in Baf3M351T, T315I and E225K implanted mice. Overall intraperitoneal treatments AN024 and AN019 were significantly better at decreasing blast cell count in all Baf3 implanted mice.

AN019 treatment in Baf3Wt implanted mice induced a complete regression of leukemic blast cells and was comparable to untreated controls. Intraperitoneal treatments were superior to oral treatments. AN019 treatment in Baf3 M351T, T315I and E225K implanted mice showed a significant decrease in blast cell count and was comparable to 12th day post-implant in ip-treated mice at day 42; ip-treated mice showed greater regression of blast cells than oral treated mice. AN024 treatment in Baf3 M351T, T315I and E225K implanted mice showed a significant decrease in blast cell count and was superior to AN019 treatment at day 42; ip-treated mice showed greater regression of blast cells than orally treated mice.

Example 4

Figure 12:
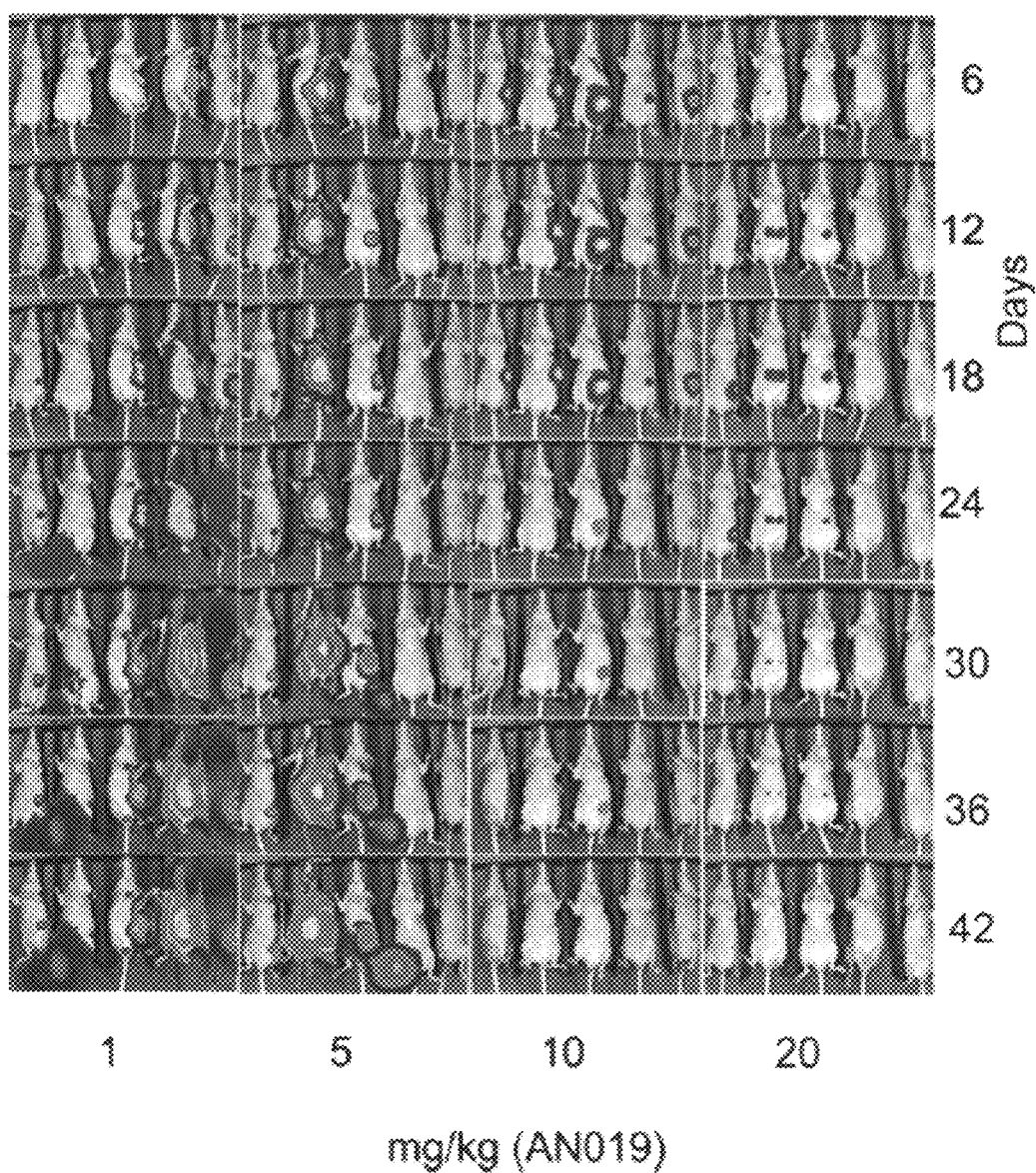
FIG. 12 illustrates that AN019 concentration at 1 mg/kg did not induce a decrease in luciferase expression, whereas 5 mg/kg caused fixation of leukemia cells at constant expression levels, and 10 and 20 mg/kg concentrations caused a decrease in luciferase expression.
Figure 13:
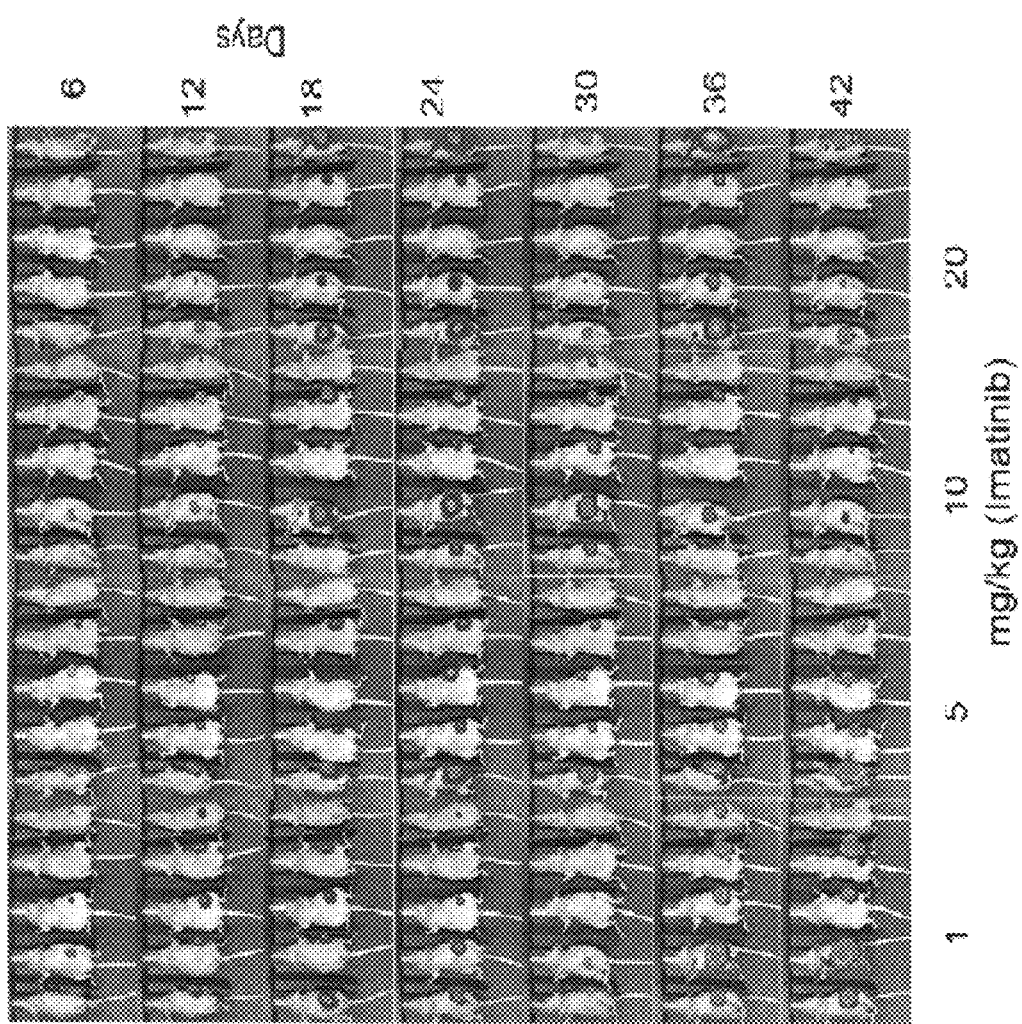
FIG. 13 illustrates that oral administration of Imatinib (1, 5, 10 and 20 mg/kg) in nude mice implanted with K562 luc human leukemia cells resulted in leukemia regression at higher concentrations. Imatinib administration at 1 mg/kg concentration did not induce a decrease in luciferase expression, whereas 10 mg/kg and 20 mg/kg did show a retardation of luciferase expression.

Response of Nude Mice Implanted with k562 Normal/Luc Human Leukemic Cells with Low Dose of AN024, AN019 and Imatinib (FIGS. 12 & 13)

Nude mice (nu/nu) were implanted with K562 cells (1×106) normal/luc via tail vein. Five mice were used per group and divided into 24 groups+2 control. All groups were implanted with K562 normal/luc cells. Of the 24 groups, 12 were used for luciferase studies whereas the other 12 were used for blood smear count studies.

Oral Administration of AN019, AN024 and Imatinib

Drugs were administered by oral gavage (2% gum acacia and 2% SLS in an aqueous suspension).

Results

Oral administration of AN019 (1, 5, 10 and 20 mg/kg) in nude mice implanted with K562 luc human leukemia cells resulted in leukemia regression at higher concentrations. AN019 concentration at 1 mg/kg did not induce a decrease in luciferase expression, whereas 5 mg/kg caused fixation of leukemia cells at constant expression levels, and 10 and 20 mg/kg concentrations caused a decrease in luciferase expression (FIG. 12). Oral administration of Imatinib (1, 5, 10 and 20 mg/kg) in nude mice implanted with K562 luc human leukemia cells resulted in leukemia regression at higher concentrations. Imatinib administration at 1 mg/kg concentration did not induce a decrease in luciferase expression, whereas 10 mg/kg and 20 mg/kg did show a retardation of luciferase expression (FIG. 13).

The study shows the superiority of AN-019 over Imatinib in leukemic regression, particularly after 24 days of treatment.

Example 5

Determination of Drug Effectiveness ($D_e$) and Drug Temporal Penetration Determination of drug effectiveness ($D_e$)

Drug effectiveness was determined using the equation, $D_e=$ $$\left[\frac{\sum alive}{\sum luc} - \frac{\sum_C alive}{\sum_C luc}\right] \div \sum_{C\text{-initial}} alive \times 100$$

Where:

$\Sigma$alive=total number of mice alive per concentration at the end of experiment times photon count, $\Sigma$luc=total number of mice alive showing luciferase expression per concentration at end of experiment and c represents control untreated animals times photon count and $\Sigma_{c\text{-initial}}$ represents the initial number of animals in control at start of experiment times photon count. The results were represented graphically as percent drug effectiveness (Table 7).

Results

Table 7 shows the drug effectiveness at various concentrations of Imatinib, AN019 and AN024 as determined from the in vivo studies. From Table 7 it is evident that AN019 behaved in a dose dependent manner, whereas Imatinib and AN024 do not, and were effective at low concentrations.

TABLE 7

| Drug | 5 mg/kg | 10 mg/kg | 20 mg/kg | 40 mg/kg |
|---|---|---|---|---|
| Imatinib $D_e$ | 10.00 | 32.00 | 13.33 | 8.00 |
| AN019 $D_e$ | 25.82 | 78.20 | 83.40 | 85.20 |
| AN024 $D_e$ | 30.00 | 85.00 | 87.00 | 90.00 |

Determination of Drug Temporal Penetrance ($T_p$)

The temporal penetrance was calculated applying the following equation, $T_p$=.

$$\frac{\left(\frac{P}{n}\right)_a - \left(\frac{P}{n}\right)_{ter}}{\left(\frac{P}{n}\right)_a - \left(\frac{P}{n}\right)_b}$$

Where:

P=photon counts at day 'a', day 'ter', or day 'b' where 'a' is the day when drug treatment was stopped and 'ter' is the day when the experiment was terminated and 'b' is the day where P is minimum after day a but before day 'ter'.

n=number of animals alive when P was measured.

The larger the value indicates greater effectiveness of the drug after stopping drug treatment, i.e. the penetrance of the drug over time.

Results

To determine the temporal penetrance of AN019, AN024 and Imatinib, nude mice were implanted with K562luc cells. The animals were imaged at 6 day intervals post transplantation. Drug treatment (AN019 20 mg/kg, AN024 20 mg/kg and Imatinib 10 mg/kg) was initiated 15 days post implantation by daily ip injections. Drug treatment was stopped on day 35 and animals were imaged till day 45, and calculated as described in methods.

By applying the equation for temporal penetrance, $T_p$ values were determined as:

AN019=2.0

AN024=2.4

Imatinib=0.8

These values of $T_p$ indicate that AN024 had activity over untreated controls and fared better than AN019 for activity over time after withdrawal of drug treatment.

Example 6

Figure 14A:
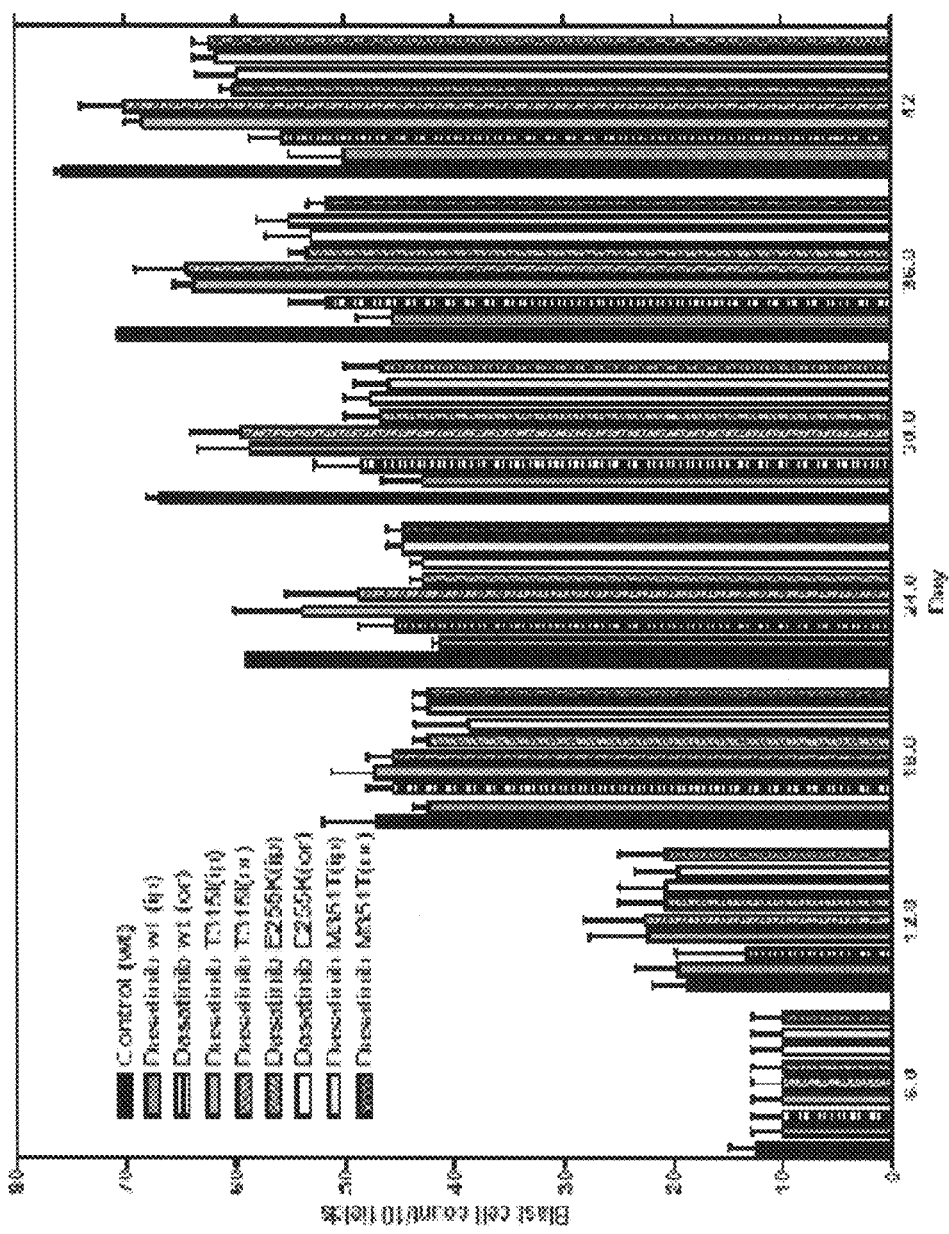
FIGS. 14A, 14B, and 14C. These figures illustrate the results of studies analogous to those illustrated in FIGS. 12 and 13 but employing the control drug Dasatinib (Example 6).
Figure 14B:
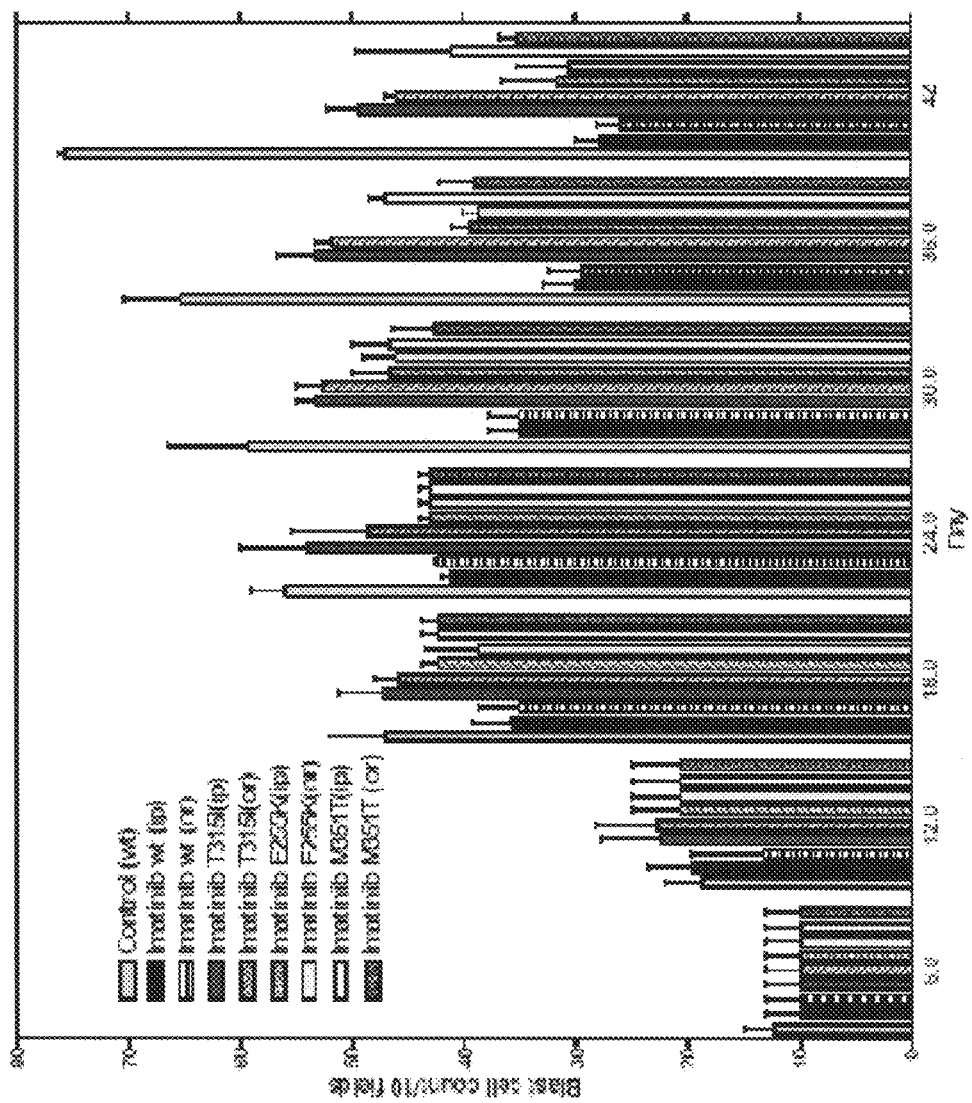
Figure 14C:
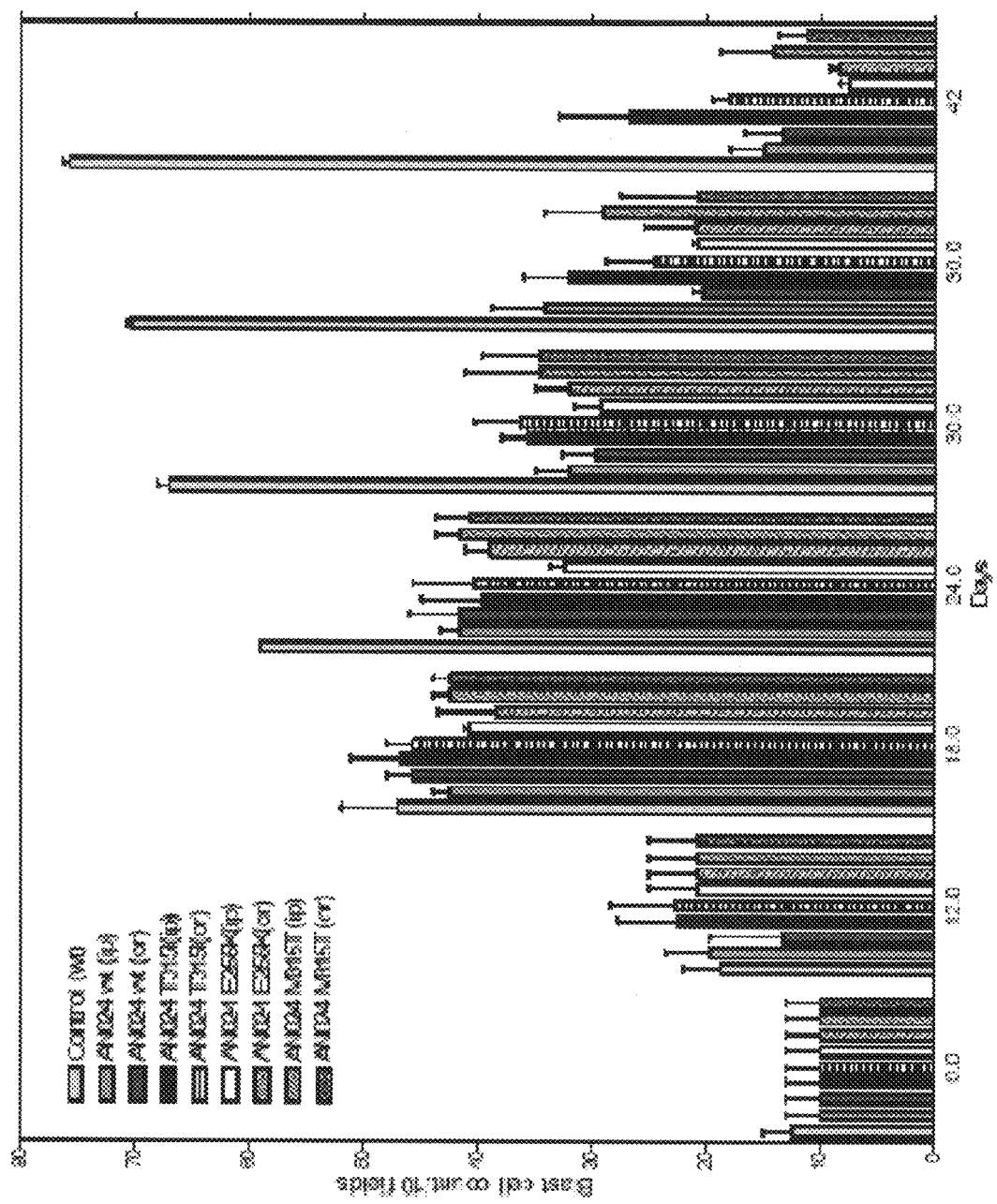

Effect of Dasatinib on Baf3 Implanted Nude Mice When Compared to AN024, AN019 and Imatinib (FIGS. 14A, 14B, and 14C)

Example 3 demonstrated the effectiveness of AN024 and AN019 in the treatment of leukemia when compared to imatinib by using Baf3 (wt, T315I, M351T and E255K) mutant cell lines. Here, we have used Dasatinib as a control drug to determine the response of Baf3 mutant cells to treatment when compared to AN019, AN024 and Imatinib.

Method

The experimental layout is given in the tabular form as follows:

| | | cell line implanted | | | |
|---|---|---|---|---|---|
| | Treatment | Wt | T315I | M351T | E255K |
| Controls (previously done) | oral | 5 | 5 | 5 | 5 |
| Dasatinib (10 mg/kg) | ip | 5 | 5 | 5 | 5 |

Nude mice were intraperitoneally implanted with Baf3 mutant cells (wt, T315I, M351T or E255K). 15 days following implantation, the mice were treated either orally or intraperitoneally with 10 mg/kg Dasatinib for 27 days. Blood was drawn from the femoral vein or tail vein every 6th day and blast cell count determined and graphically represented.

Results

On the $6^{th}$ day, blood smears of nude mice implanted with Baf3 mutant cells (wt, T315I, M351T or E255K) showed normal blast cell count, and blast cell count progressively increased as observed on day 12. Dasatinib treatment was started on day 15 post implantation. Dasatinib treatments fared no better than Imatinib. On day 42, the termination of the experiment, mice implanted with wt cells showed significant response to Dasatinib, indicating that ip treatments were superior to oral. Mice implanted with T315I and M351T cells behaved similar to controls with no significant decrease in blast cell count. Mice implanted with E255K fared only a little better than T315I implanted cells in response to Dasatinib treatment. Overall Dastinib treatment only caused retardation in leukemic progress with no significant curative effect. Blast cell count was significantly lower in the group treated with AN019. These results are illustrated in FIGS. 14A, 14B, and 14C.

Example 7

In Vitro Studies on Glioma and Breast Cell Lines (FIGS. 15-18)

Material and Methods

To determine the effect of AN019, AN024 and Temozolomide with or without radiation on glioma and breast cancer cells, cells were treated at the specified doses and determined invasion, angiogenesis and changes in certain signaling molecules.

Matrigel Invasion Assay

The in vitro invasiveness of 4910, 5310 and U87 glioma cells and MDAMB231 and ZR71 breast cancer cells in the presence of specified concentrations of compounds were assessed using a modified Boyden chamber assay. Cells were treated with these compounds for 48 h. $1\times10^6$ cells were suspended in 600 µl of serum-free medium supplemented with 0.2% BSA and placed in the upper compartment of the transwell chambers (Corning Costar Fischer Scientific Cat # 07-200-158, Pittsburgh Pa.) coated with Matrigel (0.7 mg/ml). The lower compartment of the chamber was filled with 200 µl of serum medium and the cells were allowed to migrate for 24 h. After incubation, the cells were fixed and stained with Hema-3 and quantified as previously described (Mohanam et al. 1993). The migrated cells were imaged microscopically to determine the reduction in invasiveness induced by the compounds of this invention.

Angiogenic Assay

The in vitro angiogenesis of 4910, 5310 and U87 glioma cells and MDAMB231 and ZR71 breast cancer cells in the presence of specified concentrations of compounds were determined as follows, cells (2×104/well) were seeded in 8-well chamber slides and were treated with various concentrations of test compounds. After a 24 h incubation period, the conditioned media was removed and added to a 4×104 human dermal endothelial cell (monolayer in 8-well chamber slides) and the human dermal endothelial cells were allowed to grow for 72 h. Cells were then fixed in 3.7% formaldehyde and stained with H&E and photographed.

Western Blot Analysis

Western blot analysis of 4910, 5310 and U87 glioma cells and MDAMB231 and ZR71 breast cancer cells in the presence of specified concentrations of compounds were assessed as per standard protocols. Cells were treated with AN019, AN024 or Temozolomide at the specified concentrations. 24 h after treatment, cells were collected and cell lysates extracted. Equal quantities of proteins were fractionated by SDS-PAGE. The fractionated proteins were blotted on to nylon membranes and immunoprobed for AKT, ERK and Pi3k. Breast cancer cell protein isolates were additionally immunoprobed for EGFR, ErbB1, ErbB2 and ErbB3.

Results

Matrigel Invasion Assay

The in vitro invasiveness of 4910, 5310 and U87 glioma cells and MDAMB231 and ZR71 breast cancer cells in the presence of specified concentrations of compounds were assessed using a modified Boyden chamber assay. Cells were treated with these compounds for 48 h. Table 2 shows the results from the studies of in vitro matrigel invasion assay of 4910, 5310 and U87 glioma cells and MDAMB231 and ZR71 breast cancer cells in the presence of specified concentrations of compounds, with and without radiation.

Change in the invasiveness of various cell lines is given in Table 8. From the invasion assay it is evident that AN019 and AN024 were the most effective at inhibiting invasion in a majority of the cells, both with and without radiation.

TABLE 8

| Cell line | Drug | −Radiation % Invasion | +Radiation % Invasion | ±Change in invasion after radiation |
|---|---|---|---|---|
| ZR-71 | Temozolomide | 70% | 65% | −5% |
|  | AN024 | 48% | 45% | −3% |
|  | AN019 | 33% | 19% | −14% |
| MDA-MB-231 | Temozolomide | 62% | 49% | −13% |
|  | AN024 | 43% | 47% | +4% |
|  | AN019 | 45% | 15% | −30% |
| 4910 | Temozolomide | 95% | 73% | −22% |
|  | AN024 | 56% | 39% | −17% |
|  | AN019 | 42% | 15% | −27% |
| 5310 | Temozolomide | 50% | 63% | +13% |
|  | AN024 | 27% | 32% | +5% |
|  | AN019 | 5% | 6% | +1% |
| U87 | Temozolomide | 90% | 93% | +3% |
|  | AN024 | 53% | 29% | −24% |
|  | AN019 | 18% | 18% | 0% |

Figure 15:
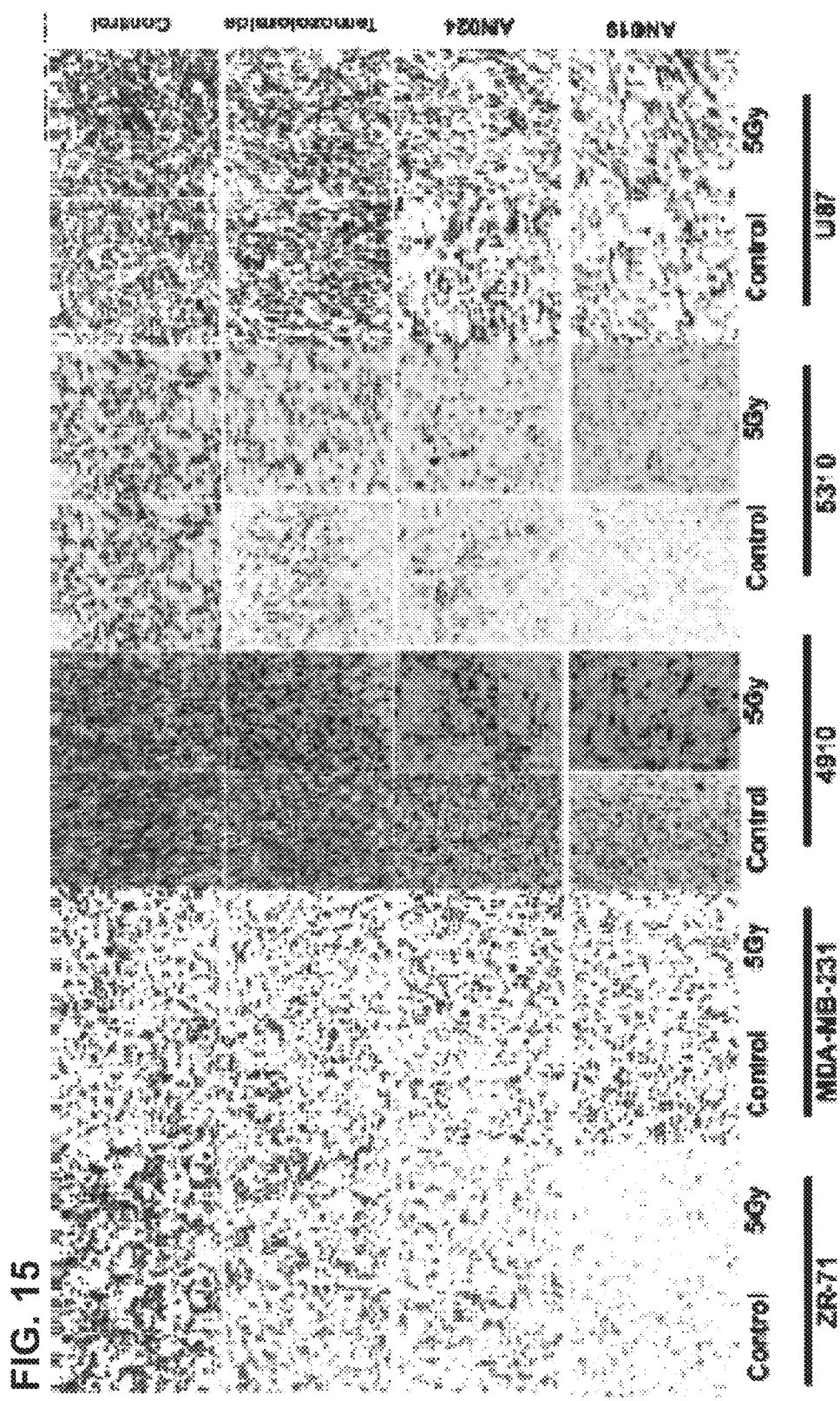
FIGS. 15 and 16. In vitro matrigel invasion assay of 4910, 5310 and U87 glioma cells and MDAMB231 and ZR71 breast cancer cells in the presence of specified concentrations of AN-019, AN-024, with and without radiation.
Figure 16:
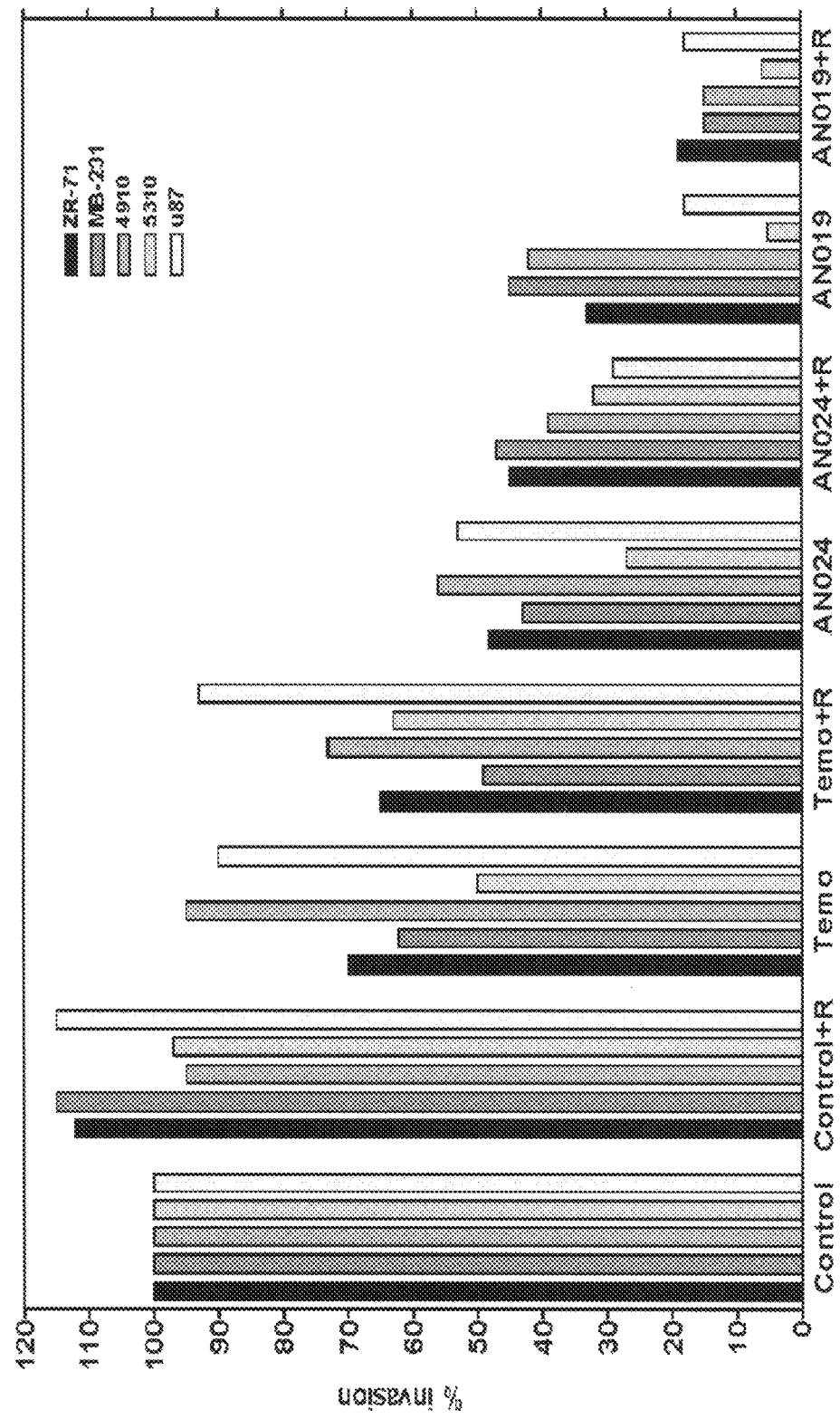

FIGS. 15 and 16 illustrate the results of the in vitro matrigel invasion assay of 4910, 5310 and U87 glioma cells and MDAMB231 and ZR71 breast cancer cells in the presence of specified concentrations of AN-019, with and without radiation.

Angiogenic Assay

From the angiogenesis assay experiments it is observed that AN019 was the most effective at inhibiting angiogenesis.

Temozolomide treatment caused complete inhibition of angiogenesis in ZR-71 cells, whereas in MDA-MB-231 cells only a slight inhibition was observed in control condition with an increase in inhibition after radiation. Glioma xenograft cells 4910 showed significant inhibition of angiogenesis both with and without radiation. In the case of 5310 cells inhibition of angiogenesis was seen in control conditions, whereas angiogenesis was promoted after radiation treatment. U87 glioma cells showed similar inhibition patterns both with and without radiation.

AN024 treatment caused complete inhibition of angiogenesis in ZR-71 cells, whereas in MDA-MB-231 cells only a slight inhibition was observed in control and radiation treatments. Glioma xenograft cells 4910 showed significant inhibition of angiogenesis both with and without radiation. In the case of 5310 cells inhibition of angiogenesis was seen in control conditions, whereas angiogenesis further inhibited after radiation treatment. U87 glioma cells showed significant retardation in angiogenesis with an increase in inhibition after radiation.

AN019 treatment caused complete inhibition of angiogenesis in ZR-71 cells, whereas in MDA-MB-231 cells a slight inhibition was observed in both control and radiation treatments. Glioma xenograft cells 4910 showed inhibition of angiogenesis similar to MDA-MB-231 cells with an increase in angiogenic inhibition after radiation. In the case of 5310 cells inhibition of angiogenesis was greater in control conditions than after radiation treatment. U87 glioma cells showed similar significant retardation in angiogenesis both with and without radiation.

Figure 17:
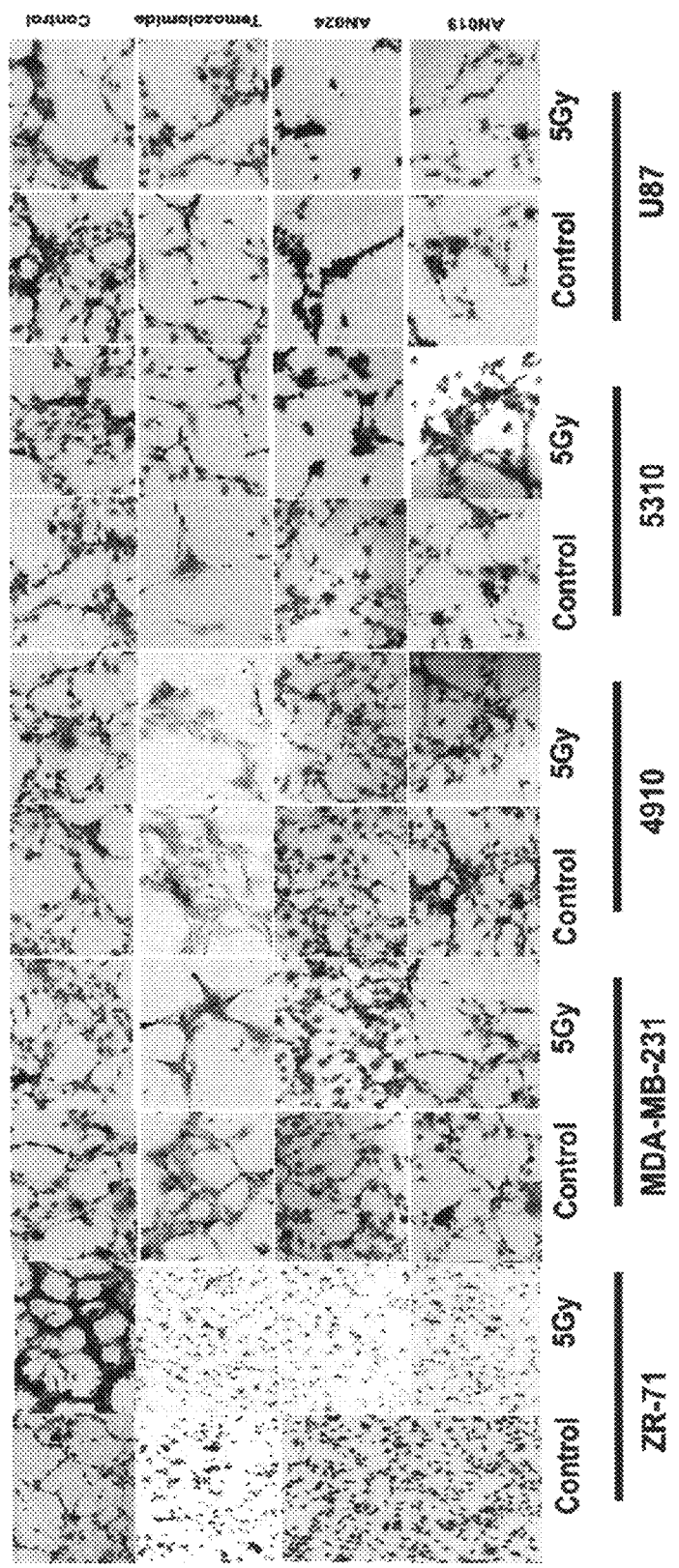
FIG. 17. In vitro angiogenic assay of 4910, 5310 and U87 glioma cells and MDAMB231 and ZR71 breast cancer cells in the presence of specified concentrations of AN-019, AN-024, with and without radiation.

FIG. 17 illustrates results obtained from the in vitro angiogenic assay of 4910, 5310 and U87 glioma cells and MDAMB231 and ZR71 breast cancer cells in the presence of specified concentrations of AN-019, with and without radiation.

Western Blot Analysis

Western blot analysis of 4910, 5310 and U87 glioma cells and MDAMB231 and ZR71 breast cancer cells in the presence of specified concentrations of compounds of this invention revealed that U87 cells did not show significant change in AKT or PI3k levels both with and without radiation, whereas a slight decrease in ERK levels was observed in AN024 treated cells and decrease was enhanced after radiation. 4910 cells behaved similar to U87 cells with a decrease in AKT levels in after AN024 treatment and the decrease in AKT levels was enhanced after radiation. In case of 5310 cells no significant observable difference was seen in ERK expression whereas AN019 treatment caused a decrease in AKT expression levels. Levels of PI3k were almost undetectable in AN019 treated cells without radiation but reappeared after radiation treatment. In case of breast cancer cells MDA-MB-231 no significant change in AKT, ERK or PI3k was observed, whereas in case of ZR71 AN019 treatment caused a decrease in AKT levels, which was enhanced after radiation. AN024 treatment did not show any significant change under unirradiated conditions, whereas after radiation AN024 treated cells showed a decrease in AKT expression. PI3k levels were absent in AN019 treatments both with and without radiation. AN024 treatment caused decrease in PI3k levels after radiation. Levels of pAKT did not change significantly in any of the treatments with or without radiation, whereas levels of pERK reduced significantly especially in cell treated with AN019 both with and without radiation, AN024 also showed reduction on pERK levels but to a lesser extent than AN019. Temozolomide treatments both with and without radiation did not show any significant change in pAKT of perk levels.

Figure 18:
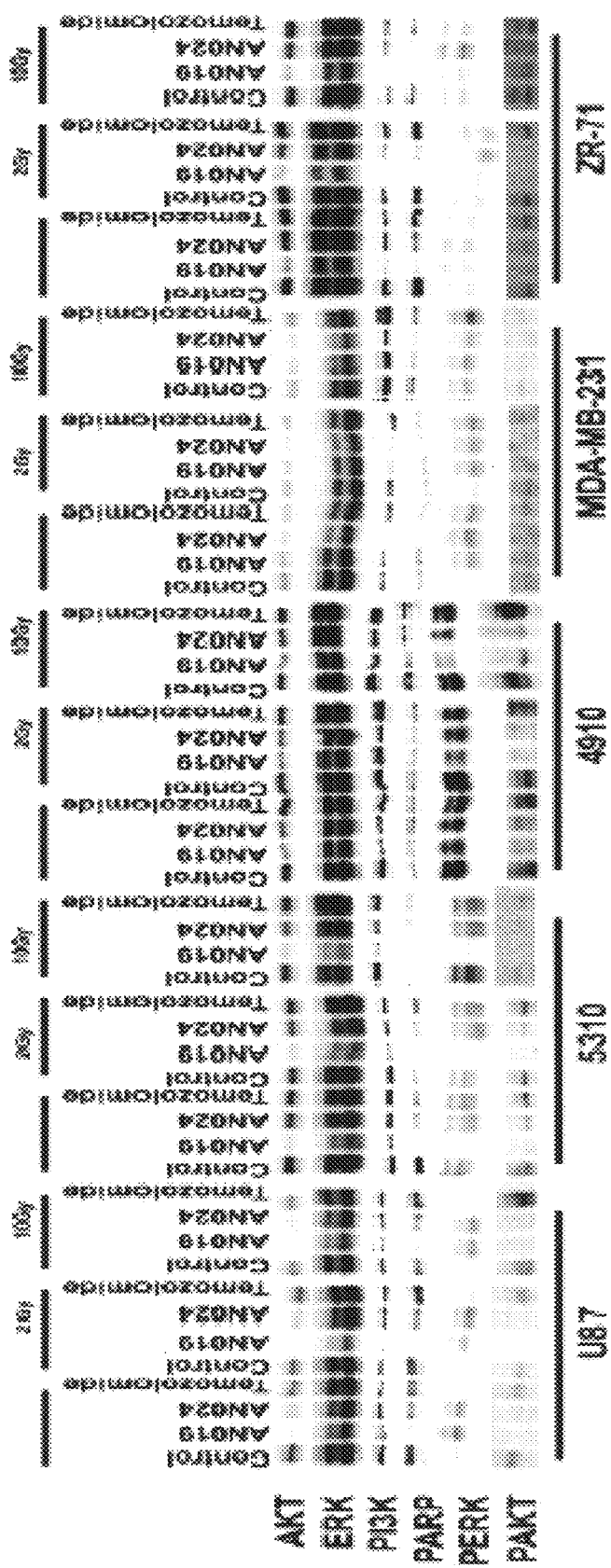
FIG. 18. Western blot analysis of 4910, 5310 and U87 glioma cells and MDAMB231 and ZR71 breast cancer cells in the presence of specified concentrations of AN-019, AN-024, with and without radiation.

FIG. 18 illustrates the results of Western blot analysis of 4910, 5310 and U87 glioma cells and MDAMB231 and ZR71 breast cancer cells in the presence of specified concentrations of AN-024, with and without radiation.

Example 8

Figure 19:
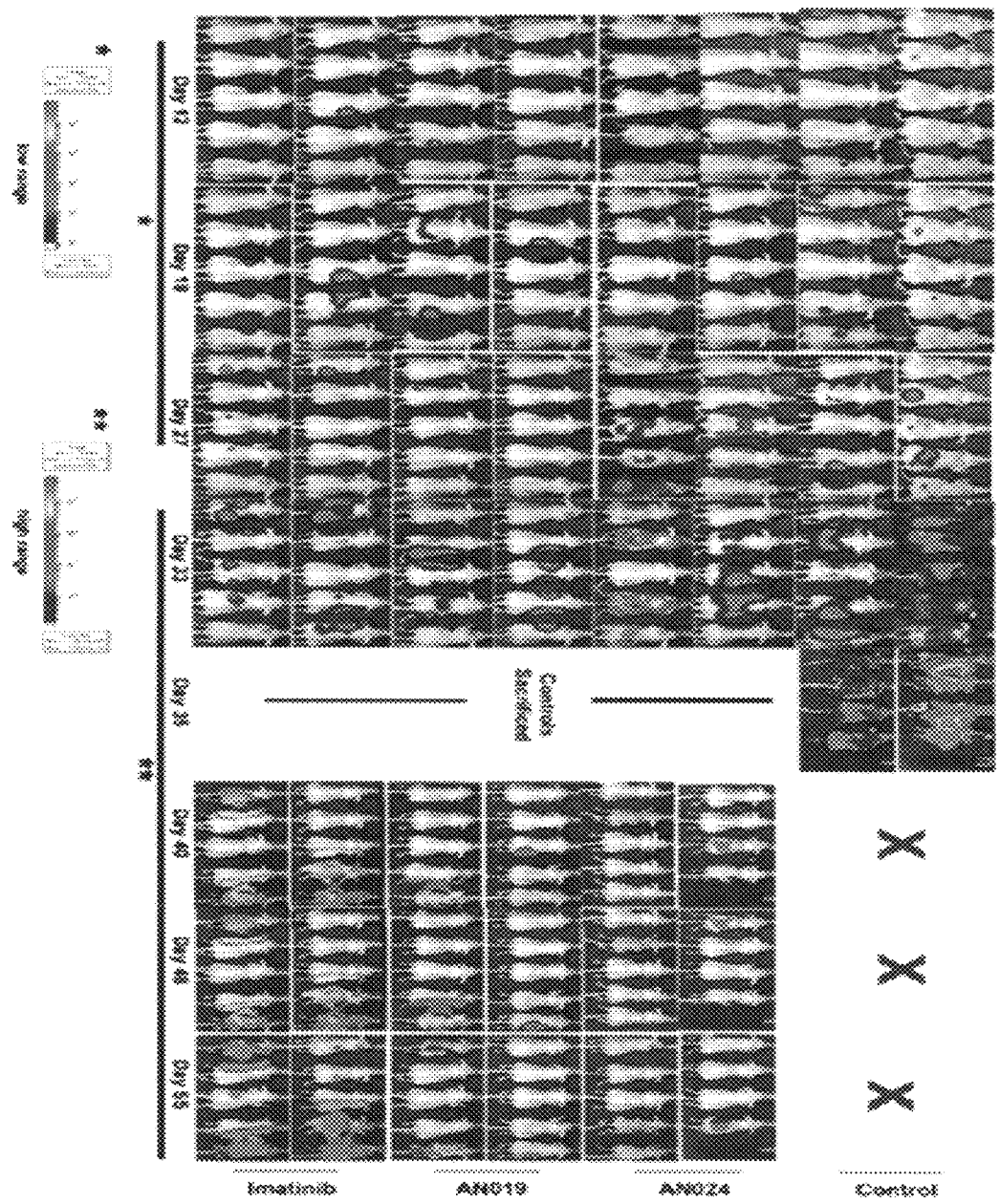
FIG. 19. Luciferase expression of K562luc implanted mice after treatment with AN024, AN019 or imatinib.
Figure 20:
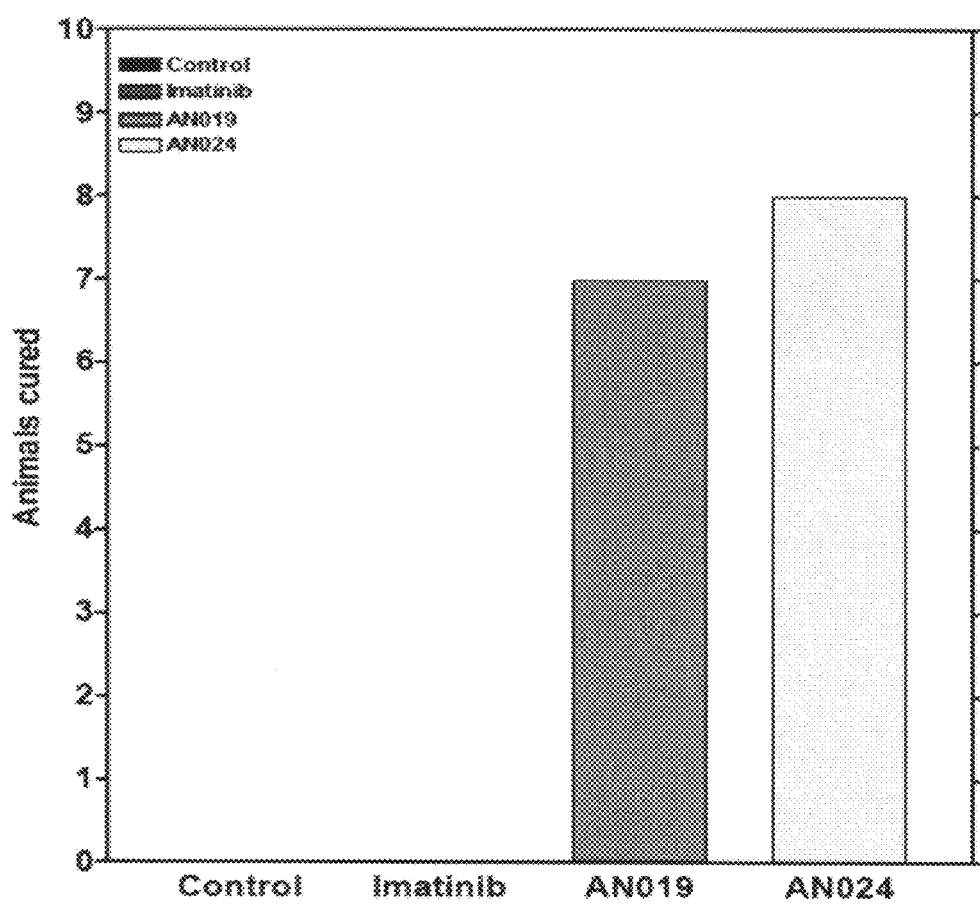
FIG. 20. Number of animals cured after treatment with AN024 or AN019 at day 58. Drug treatment was stopped at day 42, animals continued to show curative effect after treatment with AN024 and AN019 after withdrawal of drug treatment (Data based on luminescence).
Figure 21:
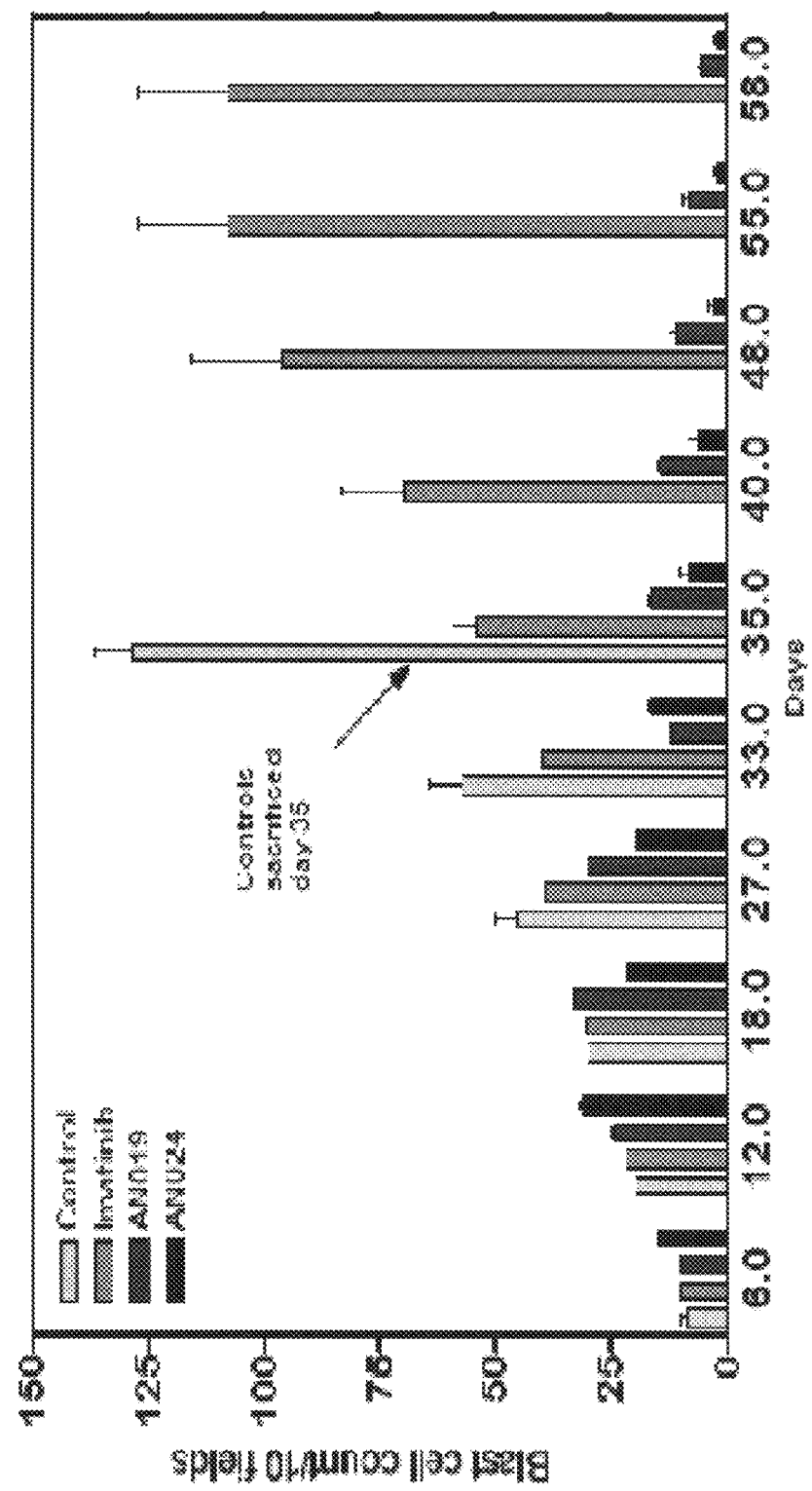
FIG. 21. Blast cell count from blood smears taken from animals at the day indicated. Drug treatment was withdrawn on day 42. AN024 and AN019 showed effectiveness after withdrawal of drug treatment. Imatinib was found to be ineffective.

Leukemic Survival Study (FIGS. 19-21)

K562 luciferase expressing cells were implanted intraperitoneally into nude mice; the mice were scanned using the xenogeny IVIS image station after ip injections of luciferin does determine implantations. Drug treatment was started as in previous studies day 15 after implantation. The animals were given treatment till day 42, after which drug treatment was stopped and survival of the animals determined as per the animal care regulations. It was observed that control animals developed leukemia and mortality had occurred on day 34 and 35, as per regulations we were advised to sacrifice the remaining 8 animals on day 35. Drug treatment was withdrawn on day 42 post implantation and survival of animals determined.

Animals treated with AN024 showed mortality on day 38, the dead animals on further inspection did not reveal spleenic enlargement and cause of death was determined to be other than leukemia, blood smears could not be taken from the dead animal. Of the 10 animals used 8 animals showed no signed of leukemia on day 55.

Animals treated with AN019 did not show any mortality and 7 of the 10 animals showed complete absence of leukemic symptoms.

Animals treated with Imatinib showed reoccurrences of leukemic symptoms after treatment withdrawal and showed mortality on day 55, 56, 57 and 58. The surviving animals did show presence of leukemic symptoms.

FIG. 19 illustrates the amount of luciferase expression of K562luc obtained from implanted mice after treatment with AN024, AN019 or imatinib.

FIG. 20 illustrates the number of animals cured after treatment with AN024 or AN019 at day 58. Drug treatment was stopped at day 42, animals continued to show curative effect after treatment with AN024 and AN019 after withdrawal of drug treatment.

FIG. 21 illustrates blast cell count from blood smears taken from animals at the day indicated. Drug treatment was withdrawn on day 42. AN024 and AN019 showed effectiveness after withdrawal of drug treatment. Imatinib was found to be ineffective.

Example 8A

Studies on $ED_{50}$, $LD_{50}$, MTD and Therapeutic Index

The following table summarizes $ED_{50}$, $LD_{50}$, early cited MTD (Maximum Tolerated Dose) and therapeutic index of the compounds of the present invention in comparison with Imatinib. Methods employed as per J. Pharmacol. Exp. Ther., (1949), 96: 96-113.

| Experimental substance | $LD_{50}$ (po) Mice (mg/Kg) | $ED_{50}$ (po) Mice (mg/Kg) | MTD Mice (mg/Kg) | Therapeutic* index - $LD_{50}/ED_{50}$ |
|---|---|---|---|---|
| Imatinib mesylate | 949 | 12 | 250 | 78.9 |
| AN-019 | 1133 | 11.5 | 500 | 98.5 |
| AN-024 | 1440 | 10 | 500 | 144 |

*Leukemic mice (K562)

Example 9

Figure 22:
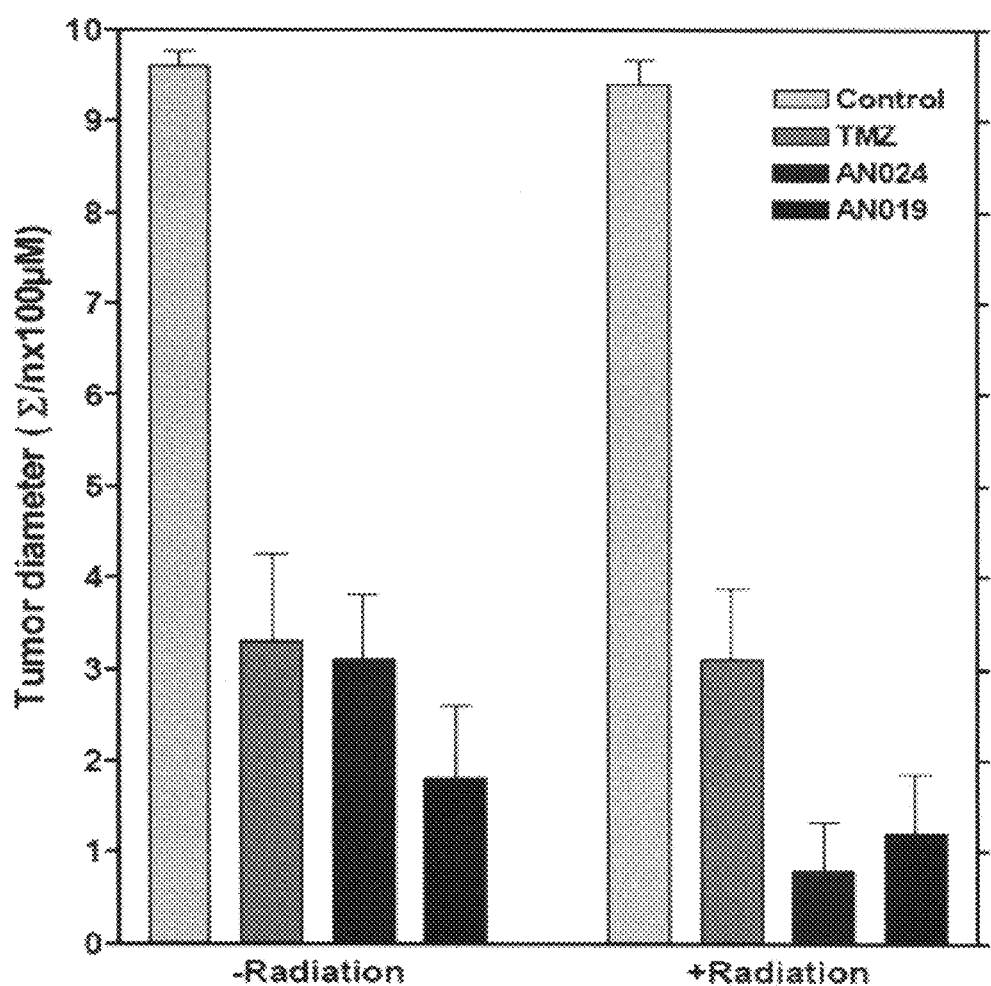
FIG. 22. Semiquantitative analysis of intracranial tumours in nude mice after treatment with TMZ, AN024 or AN019 with or without radiation (5 Gly).
Figure 23:
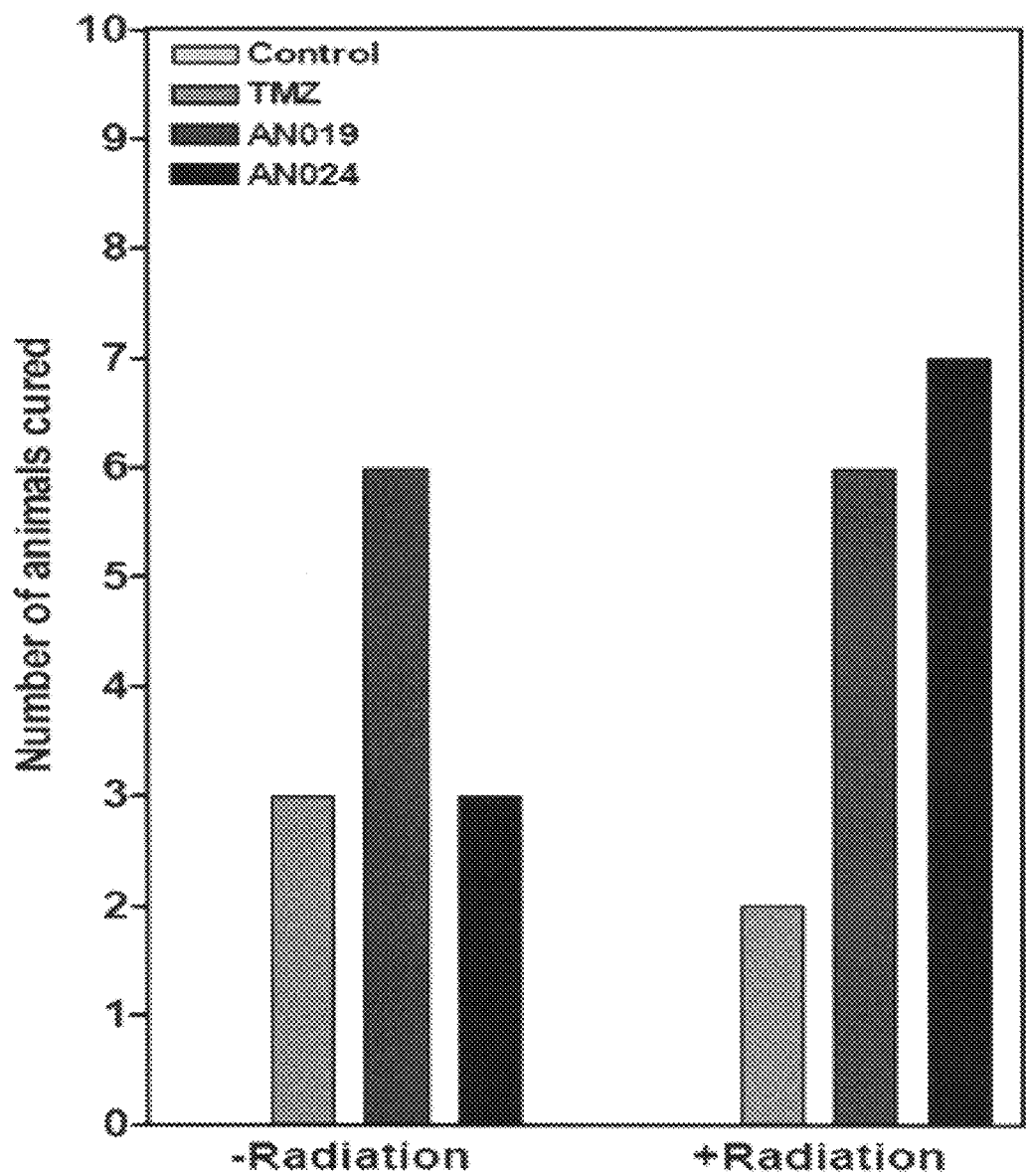
FIG. 23. Graphical representations of nude mice showing absence of intracranial tumours after drug treatment with AN-019, AN-024 and without radiation treatments.

Glioma Radiation Studies (FIGS. 22 and 23)

Nude mice were intracranially implanted with 4910 human glioma xenograft cells ($1 \times 10^6$ cells). Ten days after implantation mice were treated with AN019, AN024 or temozolomide with or without radiation (5 Gy/week). The experiment was terminated at day 40 post implantation.

From the results it was observed that 100% of control animals developed intracranial tumours and radiation alone had very little effect on tumor size reduction. Animals treated with TMZ alone showed reduction in intracranial tumours with 3 of 10 animals showing complete absence of tumours. Radiation treatment combined with TMZ administration caused a further regression in tumor size with animals showing less symptoms of intracranial pressure (arched back), in this case 2 of the 10 animals showed no observable intracranial tumor.

Animals treated with AN024 without radiation showed presence of intracranial tumours but the tumours were well defined and not showing diffuse edges as seen in controls or TMZ treatments, 3 of 10 animals were cured. After radiation treatment 7 of 10 animals were cured, the animals that showed presence of tumours showed well defined surgically respectable tumours.

Animals treated with AN019 alone showed tumours similar to AN024 treated animals and in this case both with and without radiation 6 of 10 animals were cured. It was observed that after radiation the tumor size was significantly reduced.

FIG. 22 illustrates results obtained from semiquantitative analysis of intracranial tumours in nude mice after treatment with TMZ, AN024 or AN019 with or without radiation (5 Gly).

FIG. 23 shows graphical representations of nude mice showing absence of intracranial tumours after drug treatment with AN-019, AN-024 and without radiation treatments.

The preparative synthetic and other aspects of the compounds of the present invention have been illustrated in the following examples Example 10

Preparation of Form-I (3,5-Bis trifluoromethyl)-N-[4-methyl-3-(4-pyridin-3yl-pyrimidin-2ylamino)-phenyl]-benzamide of formula-I, was prepared as per the step-IV process of Example-3 in WO2006/027795 (US 2007/0232633) as follows:

Preparation of (3,5-bistrifluoromethyl)-N-[4-methyl-3-(4-pyridin-3-yl-pyrimidin-2-ylamino)-phenyl]-benzamide (I)

Step (I): Preparation of novel (3,5-bis trifluoromethyl)-N-(4-methyl-3-nitrophenyl)-)-benzamide In the first instance, 3,5-bis trifluoro methyl benzoyl chloride which was used as one of the starting materials was prepared as follows Thionyl chloride (576.0 g, 4.8 mol) was added over a period of 15 min to a solution of 3,5-bis trifluoro methyl benzoic acid (Lancaster) (250.0 g, 0.97 mol) in chloroform (2.5 L) at room temperature. The reaction mixture was heated to reflux temperature for 1 hour. The excess of thionyl chloride was removed by co-distillation with chloroform under reduced pressure. After the end of the distillation, the resulting 3,5-bis trifluoro methyl benzoyl chloride was cooled down to room temperature and dissolved in 400 ml chloroform. A solution of 4-methyl-3-nitroaniline (92.0 g, 0.60 mol) in chloroform (1.2 L) was cooled to −5° C. and triethyl amine (304.8 g, 3.0 mol) was added. 3,5-bis trifluoro methyl benzoyl chloride in chloroform was added drop wise at −5° C. over a period of 60-75 min. The resulting suspension was stirred for 1 hr at −5° C. The suspension was distilled to a residual volume of 800 ml and filtered, washed with chilled chloroform (200 ml) and dried in vacuum to give 160.0 g of novel (3,5-bis trifluoromethyl)-N-(4-methyl-3-nitrophenyl)-)-benzamide (68%) as cream colored crystals (98.2% purity by HPLC) MR-123-130° C.

Step (II): Preparation of (3,5-bis trifluoromethyl)-N-(3-amino-4-methylphenyl)-)-benzamide A suspension of novel (3,5-bis trifluoromethyl)-N-(4-methyl-3-nitrophenyl)-benzamide (160 g, 0.41 moles) and stannous chloride (460.8 g, 2.0 moles) in absolute ethanol (850 ml) was heated to reflux temperature for 40 min. The resulting suspension was then cooled to room temperature and quenched into 5 L of ice cold water. The reaction mixture pH was adjusted to 8.0 with 4.3 L of 5% sodium hydroxide solution and extracted with 2×2 L of ethyl acetate. The ethyl acetate layer was washed successively with water and brine and dried over sodium sulfate. The ethyl acetate was distilled completely and 500 ml of hexane was added to the residue and filtered. The filtered cake was dried at high vacuum at 60° C. to give 96.0 g of novel (3,5-bis trifluoromethyl)-N-(3-amino-4-methylphenyl)-)-benzamide (65%) as yellow crystals. (98.5% purity by HPLC) MR-153-156° C.

Step (III): Preparation of (3,5-bis-trifluoromethyl)-N-(3-guanidino-4-methylphenyl)-benzamide A suspension of (3,5-bis-trifluoromethyl)-N-(3-amino-4-methylphenyl)-benzamide (90 g, 0.20 mol) in n-butanol (500 ml) was treated sequentially with concentrated Nitric acid until the pH reaches 2.5 (15.9 g) and with a solution of cyanamide (15.7 g, 0.37 mol) in water (15 ml) over a period of 30 min. The resulting reaction mixture was stirred at reflux temperature for 6 hrs. The reaction mixture was then distilled off completely under vacuum and the residue was allowed to cool down to room temperature. A mixture of 180 ml of methanol and 180 ml of IPE was added to the reaction mass and stirred at room temperature for 1 hr. The product was filtered off with suction, washed with a mixture of methanol and IPE (3×50 ml) and dried in vacuum at 60° C. to give 72 g of the nitrate salt of novel (3,5-bis-trifluoromethyl)-N-(3-guanidino-4-methylphenyl)-benzamide of the formula 62% of theory (99.2% purity by HPLC), MR-285-287° C.

Step (IV): Preparation of (3,5-bis trifluoromethyl)-N-[4-methyl-3-(4-pyridin-3-yl-pyrimidin-2-ylamino)phenyl]-benzamide (I)

A suspension of (3,5-bis-trifluoromethyl)-N-(3-guanidino-4-methylphenyl)-benzamide nitrate (70 g, 0.15 mol) in n-butanol (470 ml) under an atmosphere of nitrogen was treated successively with sodium hydroxide flakes (7.0 g, 0.18 mol) and 3-dimethylamino-1-pyridin-3-yl-propenone (28.0 g, 0.16 mol). The resulting suspension was heated to reflux temperature for 2 hrs. The reaction mixtures became a homogeneous deep orange solution and dimethylamine was removed by the distillation of n-butanol. Reaction mass was cooled down to RT and a mixture of water and chloroform (300 ml+300 ml) was added and chloroform layer was separated out. The chloroform layer was washed with water and distilled to a residual volume of 70 ml. Ethyl acetate (350 ml) was added to the reaction mass and filtered off with suction, the isolated solid was washed with ethyl acetate (2×50 ml) and water (2×50 ml) and dried in vacuum at 60° C.

Yield: 48.0 g of (3,5-bis trifluoromethyl)-N-[4-methyl-3-(4-pyridin-3-yl-pyrimidin-2-ylamino)phenyl]-benzamide of the formula I.

The compound of formula-I obtained by Step-IV process was suspended in 480 ml Chloroform and heated to 50-55° C. The reaction mass was cooled to room temperature and then cooled further to −5-0° C. The product was filtered and washed with Chloroform (250 ml). The wet cake was dried for 6 hours at 60° C. The yield was 40 gms.

Melting range −230-237° C. (DSC).

FIG. 1 of the drawings accompanying this specification shows the X-Ray Powder Diffraction (XRPD) pattern which substantially depicts a typically pure sample of form-I prepared as per the process disclosed in this Example The 2θ values and intensities are tabulated in Table 1.

Figure 4:
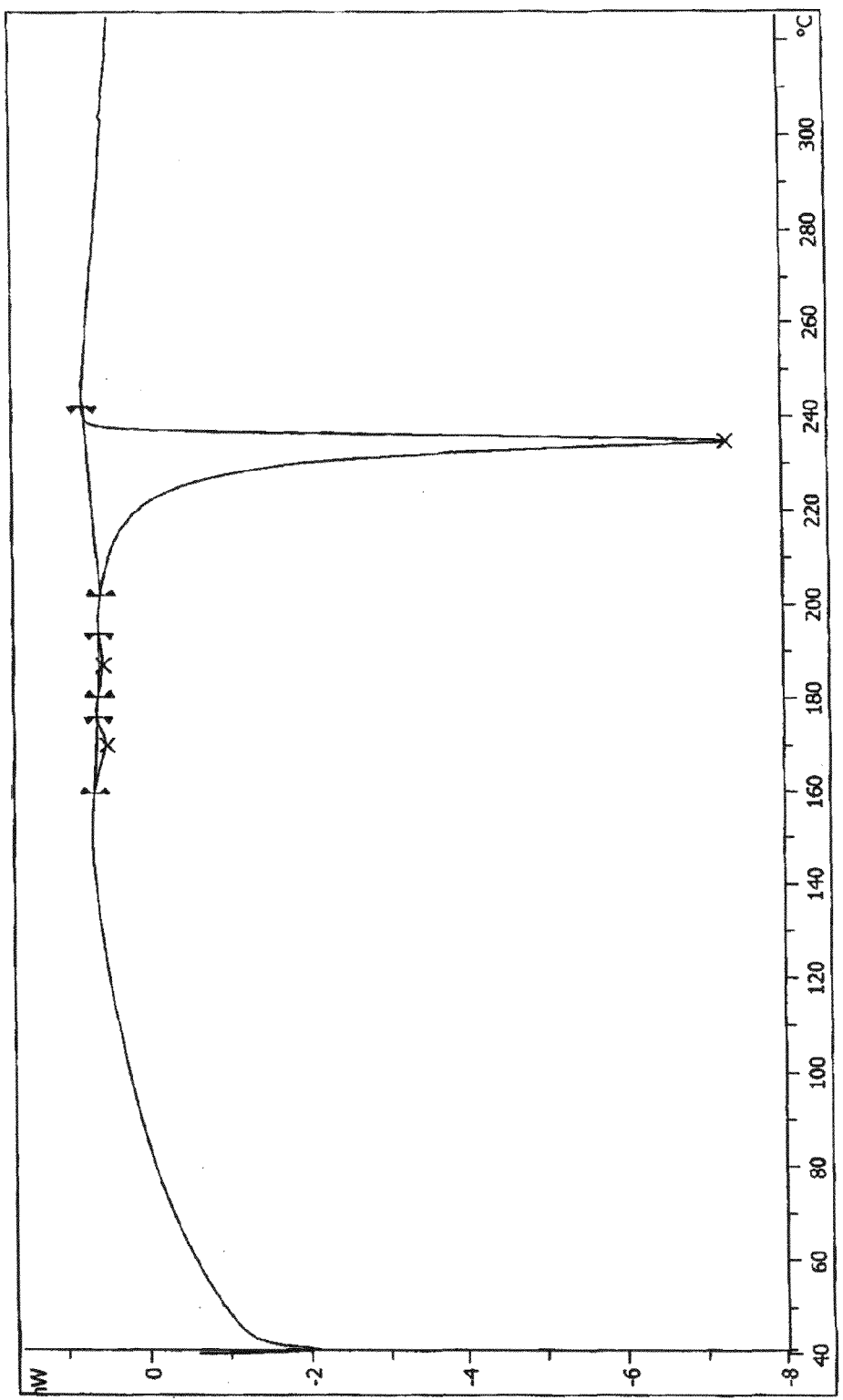
FIG. 4 shows a differential scanning calorimetry (DSC) thermogram of Form-I crystal form of the compound of formula I.

FIG. 4 shows the DSC thermogram of form-I crystal modification prepared by the process described in this Example (run from 40.0-325° C. 10.00° C./min; $N_2$ 80 ml/min).

Figure 7:
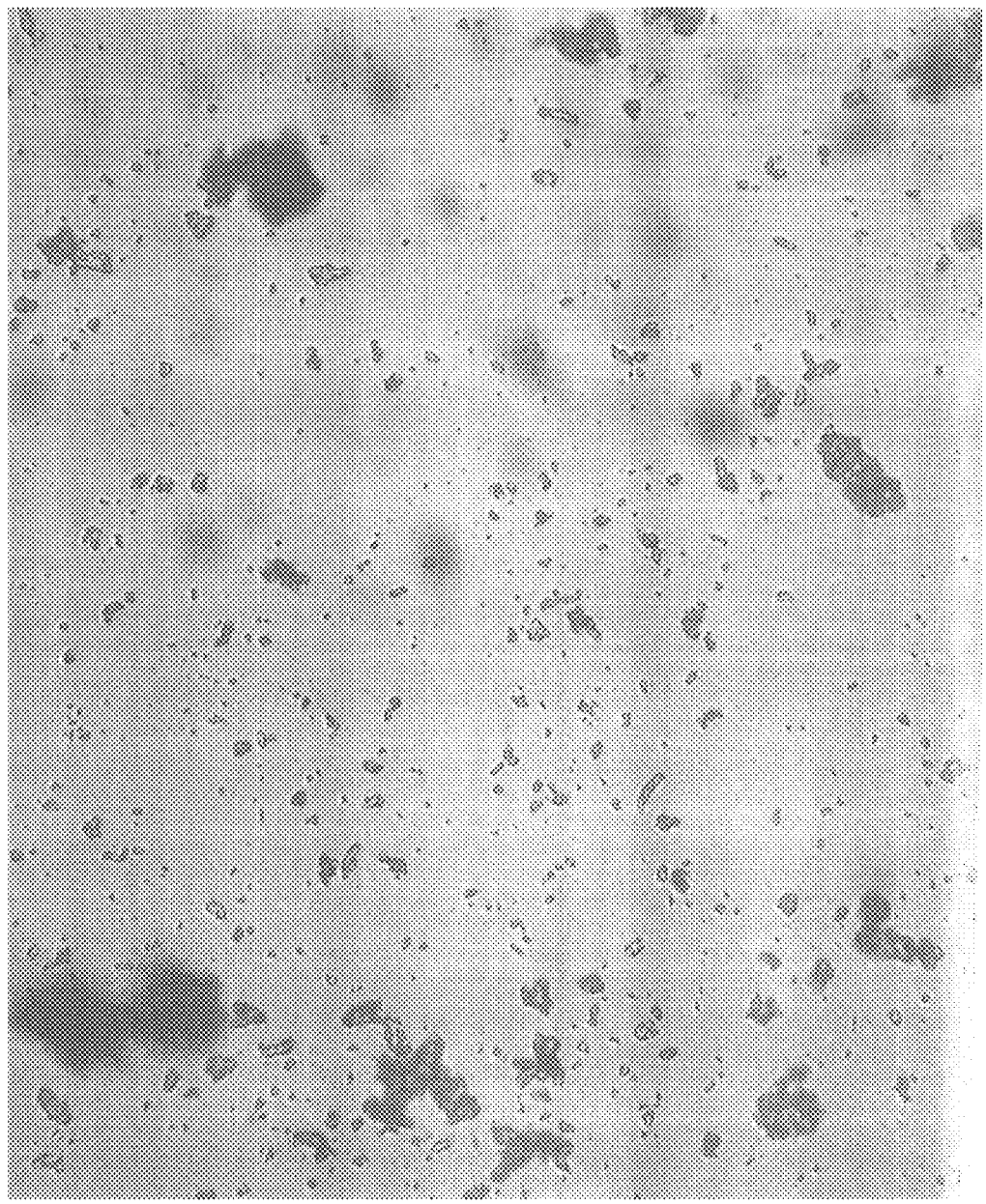
FIG. 7 shows morphology of Form-I crystal form of the compound of formula I.

FIG. 7 shows crystals of Form-I crystal modification of compound of formula (I)

Example 11

Preparation of Form-II (3,5-Bis trifluoromethyl)-N-[4-methyl-3-(4-pyridin-3yl-pyrimidin-2ylamino)phenyl]-benzamide of formula I, was prepared as per the process of Example 4 in WO2006/027795 (US 2007/0232633) as follows:

Alternative process for the Preparation of (3,5-bis trifluoromethyl)-N-[4-methyl-3-(4-pyridin-3-yl-pyrimidin-2-ylamino)-phenyl]-benzamide In the first instance, 3,5-bis trifluoro methyl benzoyl chloride which was used as one of the starting material was prepared as follows:

Thionyl chloride (2.04 kg. 17.2 mol) was added over a period of 15 min to a solution of 3,5-bis trifluoro methyl benzoic acid (855.0 g, 3.3 mol) and D.M.F. (9 ml) in chloroform (9 L) at room temperature. The reaction mixture was heated to reflux temperature for 1 hour. The excess of thionyl chloride is removed by co-distillation with chloroform under reduced pressure at 40° C. After the end of the distillation, the resulting 3,5-bis trifluoro methyl benzoyl chloride was cooled down to room temperature and dissolved in 700 ml chloroform.

A solution of N-(5-amino-2-methylphenyl)-(3-pyridyl)-2-pyrimidine amine (0.73 kgs, 2.64 mol) in chloroform (9 L) was cooled to −5° C. and triethyl amine (1.03 kg, 10.2 mol) was added. 3,5-Bis trifluoro methyl benzoyl chloride in chloroform was added drop wise at −5° C. over a period of 60-75 min. The resulting suspension was stirred for 1 hr at −5° C. The suspension was filtered, washed with D.M. water and methanol vacuum to give 1.3 kg of wet crude title compound which on recrystallization from methanol yielded 0.82 Kgs (60%) of (3,5-bis trifluoromethyl)-N-[4-methyl-3-(4-pyridin-3-yl-pyrimidin-2-ylamino)-phenyl]-benzamide (I)

The compound of formula-I obtained by the above process was suspended in 5 L methanol and heated to reflux temperature. The reaction mass was maintained at the same temperature for 30-40 minutes, cooled slowly to 40-45° C. and held at this temperature for 60 minutes. The product was filtered and washed with 0.5 L methanol at 40-45° C. The wet cake was dried for 6 hours at 60° C. Yield: 650 gms FIG. 2 of the drawings accompanying this specification shows the X-Ray Powder Diffraction (XRPD) pattern which substantially depicts a typically pure sample of Form-II prepared as per the process disclosed in this Example The 2θ values and intensities are tabulated in Table-2.

Figure 5:
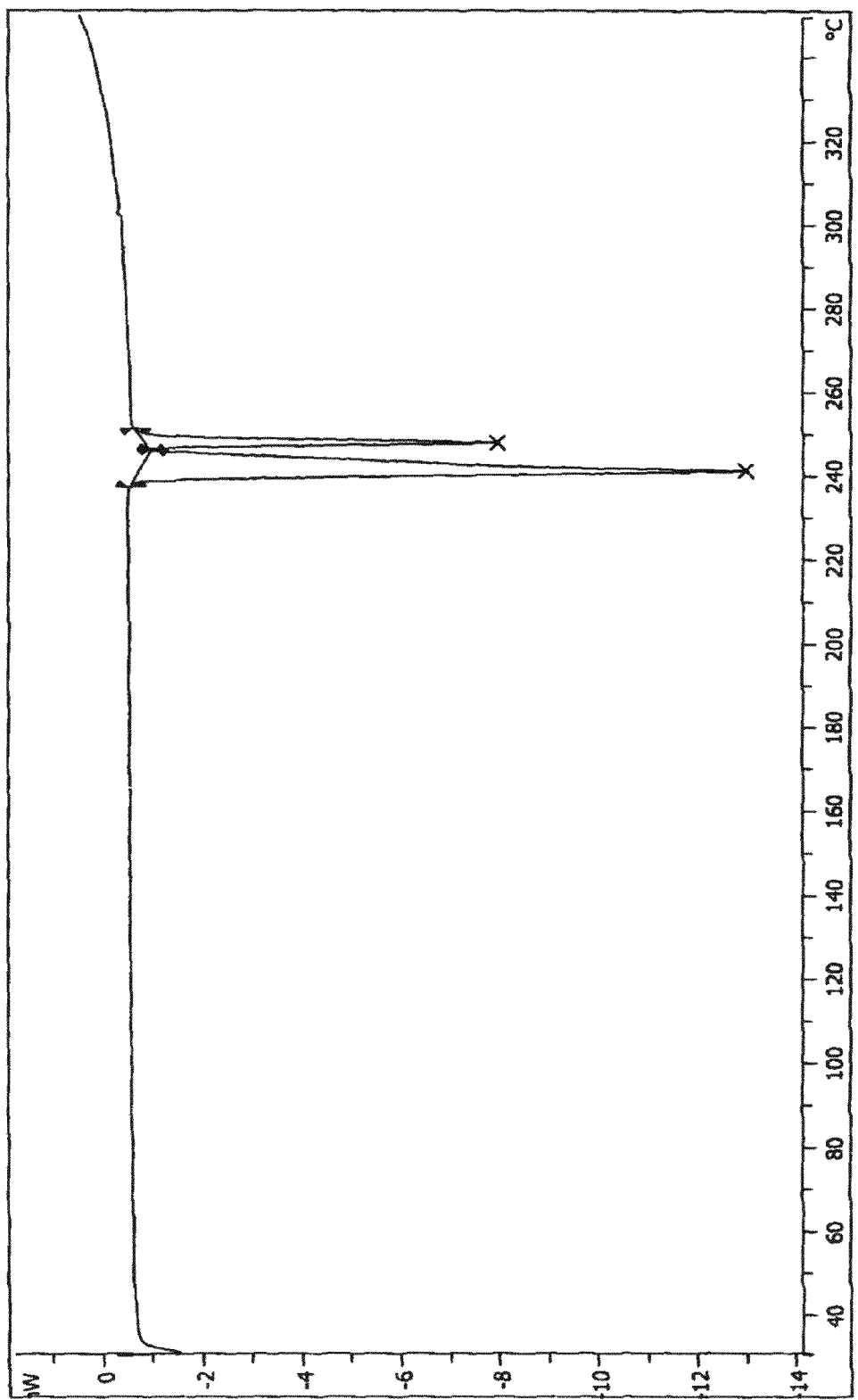
FIG. 5 shows a differential scanning calorimetry (DSC) thermogram of Form-II crystal form of the compound of formula I.

FIG. 5 shows the DSC thermogram of form-II crystal modification prepared by the process described in this Example (run from 30.0-350° C. 10.00° C./min; $N_2$ 80 ml/min).

Figure 8:
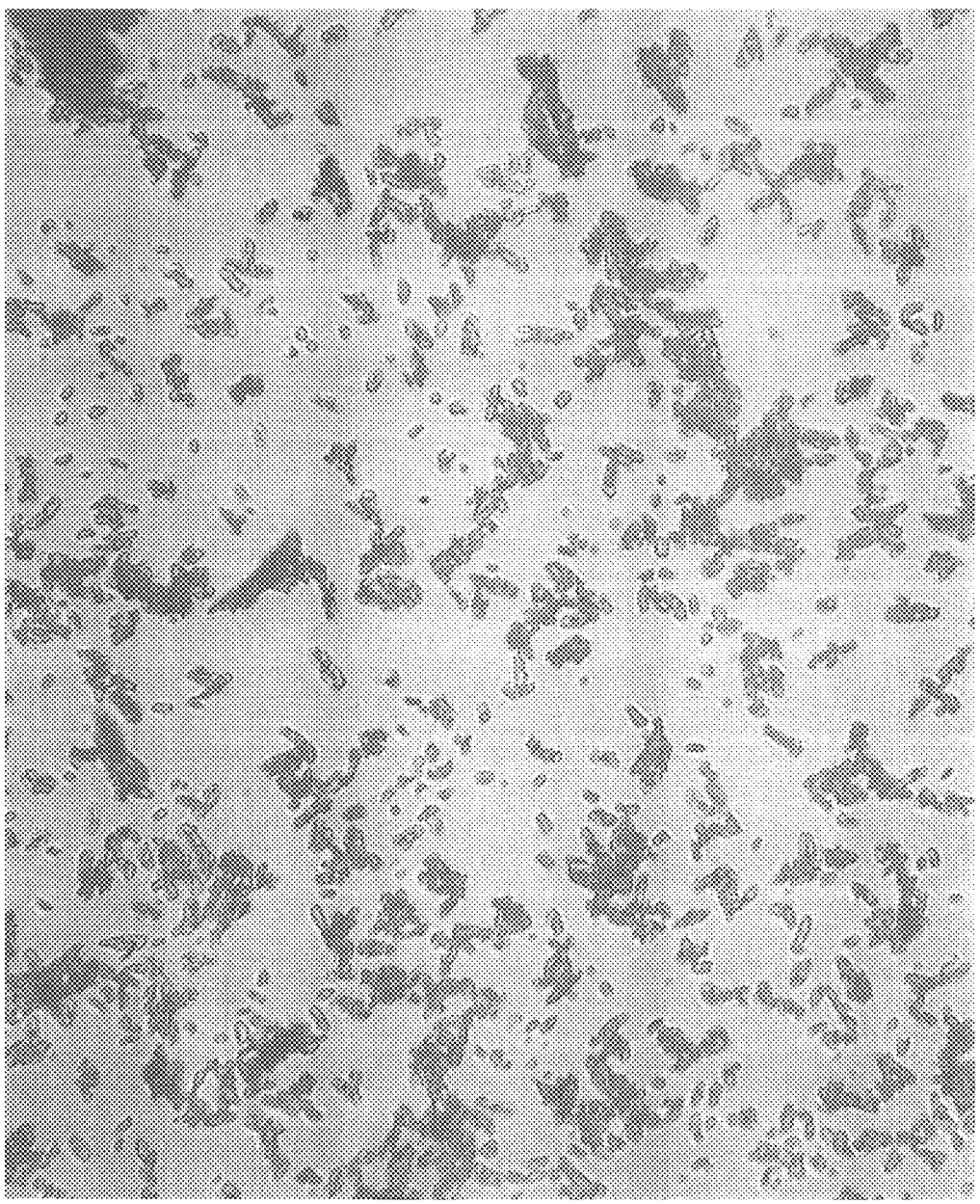
FIG. 8 shows morphology of Form-II crystal form of the compound of formula I.

FIG. 8 shows crystals of Form-II crystal modification of compound of formula (I).

Example 12

Preparation of Form-III (3,5-Bis trifluoromethyl)-N-[4-methyl-3-(4-pyridin-3yl-pyrimidin-2ylamino)-phenyl]-benzamide of formula I, was prepared as per the process of Example 4 in WO2006/027795 as mentioned in the above Example-11.

The compound of formula-I obtained by the above process was suspended in a mixture of 2.5 L Dimethyl formamide and 4.1 L acetone and heated to 50° C. The reaction mass was maintained at the same temperature for 30-40 minutes, then cooled slowly to 25-30° C. and held at the same temperature for 60 minutes. The product slurry was further cooled to −5° C. and filtered and washed with 0.8 L Acetone. The wet cake was suspended in 0.4 L acetone and heated to reflux temperature. The cooled slurry was filtered and washed with 0.4 L acetone. The wet cake was dried for 6 hours at 60° C. Yield: 500 gms.

FIG. 3 of the drawings accompanying this specification shows the X-Ray Powder Diffraction (XRPD) pattern which substantially depicts a typically pure sample of form-III prepared as per the process disclosed in this Example The 2θ values and intensities are tabulated in Table 3.

Figure 6:
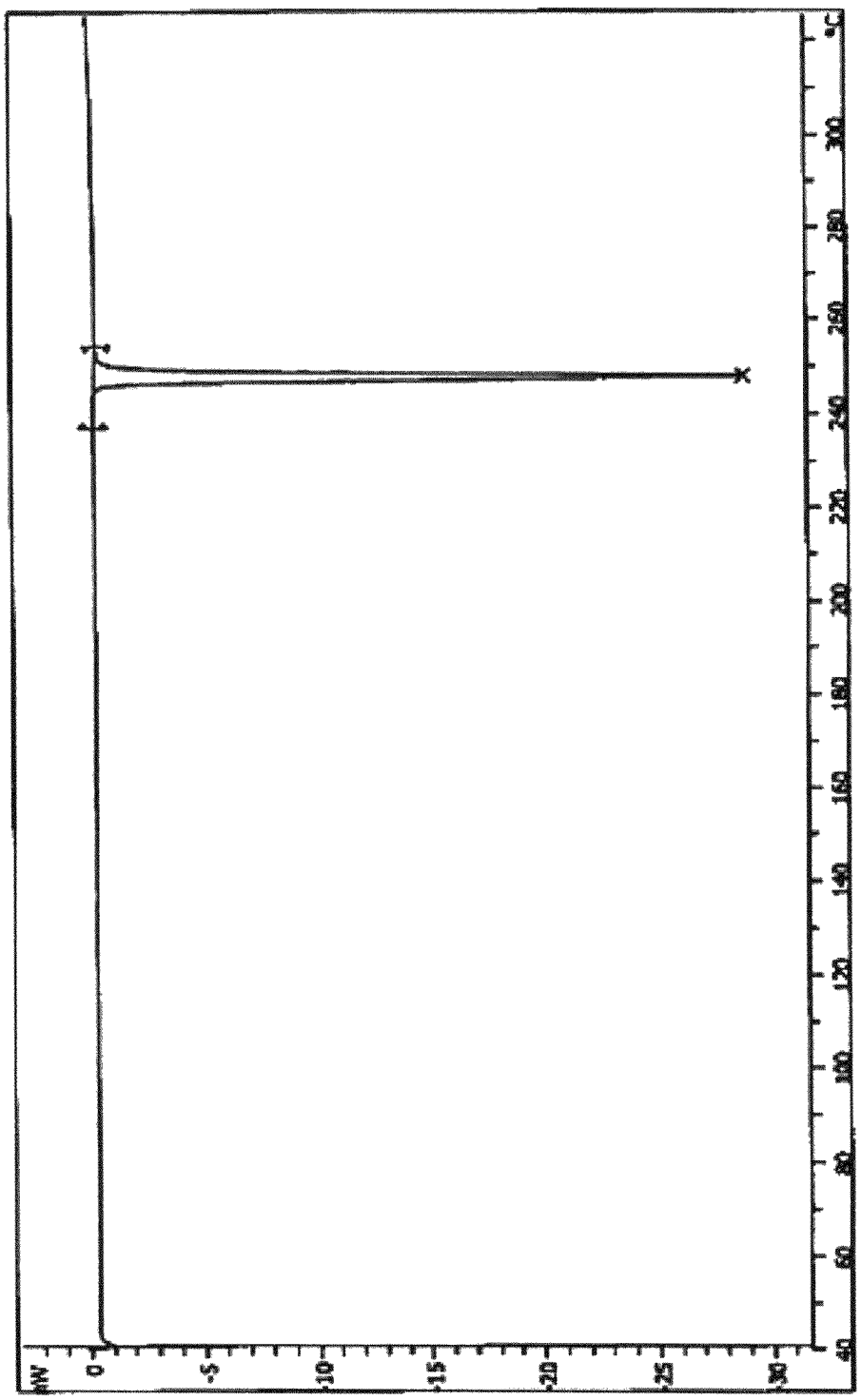
FIG. 6 shows a differential scanning calorimetry (DSC) thermogram of Form-III crystal form of the compound of formula I.

FIG. 6 shows the DSC thermogram of form-III crystal modification prepared by the process described in this Example (run from 40.0-325° C. 10.00° C./min; $N_2$ 80 ml/min).

FIG. 9 shows crystals of Form-III crystal modification of compound of formula (I).

Example-13

Preparation of Form-III (3,5-Bis trifluoromethyl)-N-[4-methyl-3-(4-pyridin-3yl-pyrimidin-2ylamino)-phenyl]-benzamide of formula I, was prepared as per the process of example-4 in WO2006/027795 as mentioned in the above example-11.

The compound of formula-I obtained by the above process was suspended in a mixture of 2.5 L dimethyl formamide and 4.1 L Hexane and heated to 50° C. The reaction mass was maintained at the same temperature for 30-40 minutes, cooled slowly to 25-30° C. and held at the same temperature for 12 hours. The product slurry was further cooled to −5° C., filtered and washed with 0.8 L Hexane. The wet cake was dried for 6 hours at 60° C. Yield: 400 gms; DSC: 248.2 (peak).

Example 14

Preparation of Form-III (3,5-Bis trifluoromethyl)-N-[4-methyl-3-(4-pyridin-3yl-pyrimidin-2ylamino)-phenyl]-benzamide of formula I, was prepared as per the process of Example 4 in WO2006/027795 as mentioned in the above Example 11.

The compound of formula-I obtained by the above process was suspended in a mixture of 2.5 L dimethyl formamide and 4.1 L toluene and heated to 50° C. The reaction mass was maintained at the same temperature for 30-40 minutes, cooled slowly to 25-30° C. and held at the same temperature for 12 hours. The slurry was cooled further to −5° C., filtered and washed with 0.8 L Toluene. The wet cake was dried for 6 hours at 60° C. Yield: 450 gms; DSC: 246.7 (peak).

Example 15

Preparation of Form-III (3,5-Bis trifluoromethyl)-N-[4-methyl-3-(4-pyridin-3yl-pyrimidin-2ylamino)-phenyl]-benzamide of formula I, was prepared as per the process of example-4 in WO2006/027795 as mentioned in the above example-11.

The compound of formula-I obtained by the above process was suspended in a mixture of 2.5 L Acetic acid and heated to 50° C. The reaction mass was maintained at the same temperature for 30-40 minutes, cooled slowly to 25-30° C. and held at the same temperature for 96 hours. The product was filtered and washed with 0.4 L chilled Acetic acid. The wet cake was dried for 6 hours at 60° C. Yield: 650 gms; DSC: 246.3 (peak).

Example 16

Preparation of Form-III

The Form-I prepared by Example-10 (40 g)was suspended in a mixture of 120 ml dimethyl formamide and 200 ml acetone and heated to 50° C. The reaction mass was maintained at the same temperature for 30-40 minutes, cooled slowly to 25-30° C. and held at the same temperature for 60 minutes. The slurry was cooled −5° C., filtered and washed with 40 ml Acetone. The wet cake was suspended in 200 ml acetone and heated to reflux temperature and maintained for 60 minutes at reflux temperature. The slurry was cooled to 25° C., filtered and washed with 40 ml acetone. The wet cake was dried for 6 hours at 60° C. Yield: 25 gms; DSC: 247.0° C. (Peak).

Example 17

Preparation of Form-III

The Form-II prepared by Example-11 (650 g) was suspended in a mixture of 1.95 L dimethyl formamide and 3.25 L acetone and heated to 50° C. The reaction mass was maintained at the same temperature for 30-40 minutes. The reaction mass was cooled slowly to 25-30° C. and maintained at the same temperature for 60 minutes. The product was filtered and washed with 0.7 L Acetone. The wet cake was suspended in 3.5 L acetone and heated to reflux temperature. The slurry was cooled to 25° C., filtered and washed with 0.7 L acetone. The wet cake was dried for 6 hours at 60° C. Yield: 395 gms; DSC: 246.5° C. (Peak).

As used herein, the term "about" refers to the variation in an amount or range that is conventional for the field of organic chemistry, for example, the typical variation that occurs in temperatures or times as measured in real world situations in the organic chemistry laboratory, scale-up, or production facility, or in evaluating anti-proliferative agents. Any range or amount used in the description of the present invention that is modified by the term "about" is also a part of the invention if not modified by the term about. For example, recitation of "about 10 to about 20" also includes recitation of "10 to 20".

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A Form-III crystal form of (3,5-bis trifluoromethyl)-N-[4-methyl-3-(4-pyridin-3yl-pyrimidin-2ylamino)-phenyl]-benzamide, wherein the Form-III crystal form has the XRPD characteristics:

| Angle [2-Theta] | d-value Angstrom | Intensity % |
|---|---|---|
| 5.909 | 14.94417 | 24.9 |
| 6.491 | 13.60517 | 66.4 |
| 8.267 | 10.68690 | 100.0 |
| 11.854 | 7.45967 | 58.2 |
| 13.181 | 6.71147 | 40.0 |
| 14.609 | 6.05866 | 50.0 |
| 15.960 | 5.54851 | 5.8 |
| 16.612 | 5.33224 | 9.5 |
| 18.826 | 4.70995 | 14.4 |
| 19.571 | 4.53226 | 52.1 |
| 21.302 | 4.16774 | 54.0 |
| 21.612 | 4.10861 | 37.7 |
| 22.160 | 4.00828 | 3.5 |
| 22.970 | 3.86869 | 23.8 |
| 23.278 | 3.81812 | 51.6 |
| 24.000 | 3.70491 | 8.7 |
| 25.112 | 3.54329 | 11.1 |
| 25.887 | 3.43895 | 3.1 |
| 26.500 | 3.36079 | 3.3 |
| 27.517 | 3.23887 | 3.4 |
| 29.476 | 3.02788 | 6.8 |
| 29.857 | 2.99011 | 8.6 |
| 30.474 | 2.93102 | 3.5 |
| 32.886 | 2.72133 | 3.2 |
| 33.559 | 2.66829 | 5.0 |
| 35.916 | 2.49836 | 3.8 |
| 39.645 | 2.27157 | 4.9 |
| 43.061 | 2.09893 | 2.6 |
| 43.748 | 2.06753 | 3.8 |
| 44.055 | 2.05383 | 3.9 |

2. The Form-III crystal form of claim 1, wherein the crystal form has melting point at or above 240° C.

3. The Form-III crystal form of claim 1, wherein the crystal form comprises about 90 to 100 wt-% the Form III crystal form.

4. A Form-I crystal form of (3,5-bis trifluoromethyl)-N-[4-methyl-3-(4-pyridin-3yl-pyrimidin-2ylamino)-phenyl]-benzamide, wherein the Form-I crystal form has the XRPD characteristics:

| Angle [2-Theta] | d-value Angstrom | Intensity % |
|---|---|---|
| 6.793 | 13.00131 | 13.9 |
| 9.823 | 8.99680 | 3.9 |
| 11.106 | 7.96069 | 54.2 |
| 13.267 | 6.66829 | 48.5 |
| 16.386 | 5.40523 | 7.0 |
| 17.941 | 4.94015 | 11.3 |
| 18.997 | 4.66785 | 13.0 |
| 19.778 | 4.48530 | 50.5 |
| 21.894 | 4.05635 | 100.0 |
| 22.396 | 3.96650 | 20.5 |
| 23.469 | 3.78750 | 19.7 |
| 24.466 | 3.63545 | 32.4 |
| 24.939 | 3.56759 | 52.6 |
| 25.525 | 3.48695 | 14.6 |
| 26.968 | 3.30351 | 10.3 |
| 28.777 | 3.09991 | 22.0 |
| 30.545 | 2.92436 | 14.8 |
| 33.011 | 2.71129 | 11.0 |

5. A Form-II crystal form of (3,5-bis trifluoromethyl)-N-[4-methyl-3-(4-pyridin-3yl-pyrimidin-2ylamino)-phenyl]-benzamide, wherein the Form-II crystal form has the XRPD characteristics:

| Angle [2-Theta] | d-value Angstrom | Intensity % |
|---|---|---|
| 6.500 | 13.58651 | 12.2 |
| 10.816 | 8.17295 | 100.0 |
| 12.094 | 7.31197 | 3.4 |
| 12.988 | 6.81061 | 49.7 |
| 16.120 | 5.49381 | 6.0 |
| 17.669 | 5.01562 | 10.9 |
| 19.521 | 4.54367 | 41.7 |
| 21.675 | 4.09687 | 39.9 |
| 22.083 | 4.02198 | 17.1 |
| 23.230 | 3.82602 | 21.9 |
| 24.264 | 3.66523 | 17.8 |
| 24.639 | 3.61023 | 8.5 |
| 28.460 | 3.13371 | 4.8 |
| 29.328 | 3.04290 | 2.3 |
| 30.256 | 2.95165 | 4.1 |
| 32.746 | 2.73261 | 3.5 |
| 32.746 | 2.73261 | 3.5 |
| 34.035 | 2.63201 | 3.1 |
| 35.590 | 2.52050 | 1.5 |
| 39.660 | 2.27072 | 1.9 |
| 42.123 | 2.14346 | 2.5 |
| 44.193 | 2.04777 | 1.7 |

6. A pharmaceutical composition comprising a pharmaceutically acceptable excipient and a Form-III crystal form of (3,5-bis trifluoromethyl)-N-[4-methyl-3-(4-pyridin-3yl-pyrimidin-2ylamino)-phenyl]-benzamide, wherein the Form-III crystal form has the XRPD characteristics:

| Angle [2-Theta] | d-value Angstrom | Intensity % |
|---|---|---|
| 5.909 | 14.94417 | 24.9 |
| 6.491 | 13.60517 | 66.4 |

-continued

| Angle [2-Theta] | d-value Angstrom | Intensity % |
| --- | --- | --- |
| 8.267 | 10.68690 | 100.0 |
| 11.854 | 7.45967 | 58.2 |
| 13.181 | 6.71147 | 40.0 |
| 14.609 | 6.05866 | 50.0 |
| 15.960 | 5.54851 | 5.8 |
| 16.612 | 5.33224 | 9.5 |
| 18.826 | 4.70995 | 14.4 |
| 19.571 | 4.53226 | 52.1 |
| 21.302 | 4.16774 | 54.0 |
| 21.612 | 4.10861 | 37.7 |
| 22.160 | 4.00828 | 3.5 |
| 22.970 | 3.86869 | 23.8 |
| 23.278 | 3.81812 | 51.6 |
| 24.000 | 3.70491 | 8.7 |
| 25.112 | 3.54329 | 11.1 |
| 25.887 | 3.43895 | 3.1 |
| 26.500 | 3.36079 | 3.3 |
| 27.517 | 3.23887 | 3.4 |
| 29.476 | 3.02788 | 6.8 |
| 29.857 | 2.99011 | 8.6 |
| 30.474 | 2.93102 | 3.5 |
| 32.886 | 2.72133 | 3.2 |
| 33.559 | 2.66829 | 5.0 |
| 35.916 | 2.49836 | 3.8 |
| 39.645 | 2.27157 | 4.9 |
| 43.061 | 2.09893 | 2.6 |
| 43.748 | 2.06753 | 3.8 |
| 44.055 | 2.05383 | 3.9. |

7. A process for preparing a Form-III crystal form of (3,5-bis trifluoromethyl)-N-[4-methyl-3-(4-pyridin-3yl-pyrimidin-2ylamino)-phenyl]-benzamide, the process comprising:
treating the (3,5-bis trifluoromethyl)-N-[4-methyl-3-(4-pyridin-3yl-pyrimidin-2ylamino)-phenyl]-benzamide in a Form-I or Form-II crystal form with acetic acid, a mixture of dimethyl formamide and acetone, a mixture of dimethyl formamide and hexane, or a mixture of dimethyl formamide and toluene; and
subsequently treating the once treated compound with acetic acid, acetone, hexane, or toluene;
wherein the Form-III crystal form has the XRPD characteristics:

| Angle [2-Theta] | d-value Angstrom | Intensity % |
| --- | --- | --- |
| 5.909 | 14.94417 | 24.9 |
| 6.491 | 13.60517 | 66.4 |
| 8.267 | 10.68690 | 100.0 |
| 11.854 | 7.45967 | 58.2 |
| 13.181 | 6.71147 | 40.0 |
| 14.609 | 6.05866 | 50.0 |
| 15.960 | 5.54851 | 5.8 |
| 16.612 | 5.33224 | 9.5 |
| 18.826 | 4.70995 | 14.4 |
| 19.571 | 4.53226 | 52.1 |
| 21.302 | 4.16774 | 54.0 |
| 21.612 | 4.10861 | 37.7 |
| 22.160 | 4.00828 | 3.5 |
| 22.970 | 3.86869 | 23.8 |
| 23.278 | 3.81812 | 51.6 |
| 24.000 | 3.70491 | 8.7 |
| 25.112 | 3.54329 | 11.1 |
| 25.887 | 3.43895 | 3.1 |
| 26.500 | 3.36079 | 3.3 |
| 27.517 | 3.23887 | 3.4 |
| 29.476 | 3.02788 | 6.8 |
| 29.857 | 2.99011 | 8.6 |
| 30.474 | 2.93102 | 3.5 |
| 32.886 | 2.72133 | 3.2 |
| 33.559 | 2.66829 | 5.0 |
| 35.916 | 2.49836 | 3.8 |

-continued

| Angle [2-Theta] | d-value Angstrom | Intensity % |
| --- | --- | --- |
| 39.645 | 2.27157 | 4.9 |
| 43.061 | 2.09893 | 2.6 |
| 43.748 | 2.06753 | 3.8 |
| 44.055 | 2.05383 | 3.9. |

8. The process of claim 7, comprising:
treating the compound of formula I in a Form-I or Form-II crystal form with acetic acid; and,
subsequently treating the once treated compound with acetic acid.

9. The process of claim 7, comprising:
treating the compound of formula I in a Form-I or Form-II crystal form with a mixture of dimethyl formamide and acetone; and,
subsequently treating the once treated compound with acetone.

10. The process of claim 7, comprising:
treating the compound of formula I in a Form-I or Form-II crystal form with a mixture of dimethyl formamide and hexane; and,
subsequently treating the once treated compound with hexane.

11. The process of claim 7, comprising:
treating the compound of formula I in a Form-I or Form-II crystal form with a mixture of dimethyl formamide and toluene; and,
subsequently treating the once treated compound with toluene.

12. A method of preparing compound of formula I:

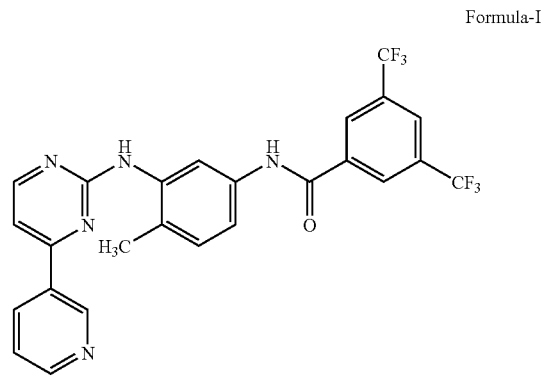

Formula-I

Development code: AN-019 the method comprising:
providing a 3,5-bis trifluoro methyl benzoyl chloride;
condensing 4-methyl-3-nitro-aniline with the 3,5-bis trifluoro methyl benzoyl chloride at about 0 to about −10° C. in chlorohydrocarbon solvent with addition of a basic compound to obtain a ((3,5-bis trifluoromethyl)-N-(4-methyl-3-nitrophenyl)-)-benzamide;
reducing the ((3,5-bis trifluoromethyl)-N-(4-methyl-3-nitrophenyl)-)-benzamide with stannous chloride and concentrated HCl at reflux temperature for about 0.5 to about 1 hour to obtain a (3,5-bis trifluoromethyl)-N-(3-amino-4-methylphenyl)-)-benzamide;

condensing the (3,5-bis trifluoromethyl)-N-(3-amino-4-methylphenyl)-)-benzamide with aqueous cyanamide at reflux temperature in n-butanol to obtain a (3,5-bis-trifluoromethyl)-N-(3-guanidino-4-methylphenyl)-benzamide;

condensing the (3,5-bis-trifluoromethyl)-N-(3-guanidino-4-methylphenyl)-benzamide with 3-dimethylamino-1-pyridin-3-yl-propenone in presence of base at reflux temperature to obtain the compound of formula (I).

* * * * *